United States Patent
James

(10) Patent No.: US 8,759,290 B2
(45) Date of Patent: Jun. 24, 2014

(54) ORAL GLUCAGON-LIKE PEPTIDE CONJUGATES FOR METABOLIC DISEASES

(75) Inventor: Kenneth D. James, Mebane, NC (US)

(73) Assignee: Biocon Limited (IN)

( * ) Notice: Subject to any disclaimer, the term of this patent is extended or adjusted under 35 U.S.C. 154(b) by 1292 days.

(21) Appl. No.: 12/090,306

(22) PCT Filed: Oct. 18, 2006

(86) PCT No.: PCT/US2006/040868
§ 371 (c)(1),
(2), (4) Date: Sep. 16, 2008

(87) PCT Pub. No.: WO2007/047834
PCT Pub. Date: Apr. 26, 2007

(65) Prior Publication Data
US 2009/0221485 A1    Sep. 3, 2009

Related U.S. Application Data

(60) Provisional application No. 60/727,691, filed on Oct. 18, 2005.

(51) Int. Cl.
*A61K 38/17* (2006.01)
*A61K 38/26* (2006.01)

(52) U.S. Cl.
USPC .......................... 514/11.7; 530/324; 514/7.2

(58) Field of Classification Search
None
See application file for complete search history.

(56) References Cited

FOREIGN PATENT DOCUMENTS

WO    WO 2004/022004    *    3/2004    ............. A61K 38/00
WO    WO 2005058954 A1 *    6/2005

OTHER PUBLICATIONS

Holz, G.H. & Chepurny, O.G. (2003) Glucagon-Like Peptide-1 Synthetic Analogs: New Therapeutic Agents for Use in the Treatment of Diabetes Mellitus. Curr Med Chem. 10(22): 2471-2483.*
Caliceti & Veronese (2003) P harmacokinetic and biodistribution properties of poly(ethylene glycol)-protein conjugates. Advanced Drug Delivery Reviews 55, 1261-1277.*
Naslund et a. "Energy intake and appetite are suppressed by glucagon-like peptide-1 (GLP-1) in obese men." International Journal of Obesity, 199, vol. 23, pp. 304-311, (1999).
Naslund et a. "Energy intake and appetite are suppressed by glucagon-like peptide-1 (GLP-1) in obese men." International Journal of Obesity, 199, vol. 23, pp. 304-311. Date: 1999.
Barragan, J. M., R. E. Rodriguez, et al. Interactions of exendin-(9-39) with the effects of glucagon-like peptide-1(7-36) amide and of exendin-4 on arterial blood pressure and heart rate in rats. *Regulatory Peptides* (1996) 67(1): 63-68.
Drucker, Daniel J. Biological Actions and Therapeutic Potential of the Glucagon-Like Peptides. *Gastroenterology*. Feb. 2002 ; 122(2):531-544.
Deacon, Carolyn F. et al. Both Subcutaneously and Intravenously Administered Glucagon-like Peptide I are rapidly degraded from the NH2-terminus in Type II Diabetic Patients and in Healthy Subjects. *Diabetes*. Sep. 1995; 44(9):1126-31.
Drucker, Daniel, J. Development of Glucagon-Like Peptide-1-Based Pharmaceuticals as Therapeutic Agents for the Treatment of Diabetes. *Curr Pharm Des*. Sep. 2001;7(14):1399-1412.
Drucker, Daniel J. Minireview: The Glucagon-Like Peptides. *Endocrinology*. Feb. 2001; 142(2):521-7.
Eng, J. and C. Eng Exendin-3 and Exendin-4 Are Insulin Secretagogues. *Regulatory Peptides* (1992) 40(2): 142-142.
Eng, J., W. A. Kleinman, et al. Isolation and Characterization of Exendin-4, an Exendin-3 Analog, from Heloderma-Suspectum Venom—Further Evidence for an Exendin Receptor on Dispersed Acini from Guinea-Pig Pancreas. *Journal of Biological Chemistry* 267 (1992). (11): 7402-7405.
Lee, Sang-Heon et al. Synthesis, Characterization, and Pharmacokinetic Studies of PEGylated Glucagon-like Peptide-1. *Bioconjugate Chem*. 2005, 16, 377-382.
Malhotra, R., L. Singh, et al. Exendin-4, a New Peptide from Heloderma-Suspectum Venom, Potentiates Cholecystokinin-Induced Amylase Release from Rat Pancreatic Acini. (1992) *Regulatory Peptides* 41(2): 149-156.
Nauck, Michael A. et al. Glucagon-Like Peptide 1 and its Derivatives in the Treatment of Diabetes. *Regulatory Peptides*. Jul. 2005; 128:135-48.
Orskov, Cathrine et al. Tissue and Plasma Concentrations of Amidated and Glycine-Extended Glucagon-Like Peptide I in Humans. *Diabetes*. Apr. 1994;43(4):535-9.
Orskov, Cathrine et al. Biological Effects and Metabolic Rates of Glucagonlike Peptide-1 7-36 Amide and Glucagonlike Peptide-1 7-37 in Healthy Subjects are Indistinguishable. *Diabetes*. May 1993;42(5):658-61.

* cited by examiner

*Primary Examiner* — Vanessa L Ford
*Assistant Examiner* — Sandra Dillahunt
(74) *Attorney, Agent, or Firm* — Marianne Fuierer; Moore & Van Allen, PLLC

(57) ABSTRACT

The present invention relates to the field of metabolic compound conjugates, methods of forming said conjugates and uses of these conjugates in the treatment of diabetes and conditions related to this condition. The metabolic compound conjugates of this invention include a metabolic peptide having a glucagon-like peptide (GLP-1) receptor binding motif for action on a GLP-1 receptor and at least one oligomer conjugation site for binding with at least one oligomer, wherein the oligomer includes a polyethylene glycol moiety (PEG), and/or alkyl moiety.

7 Claims, 2 Drawing Sheets

ORAL GLUCAGON-LIKE PEPTIDE CONJUGATES FOR METABOLIC DISEASES

CROSS-REFERENCE TO RELATED APPLICATIONS

This application is filed under the provisions of 35 U.S.C. §371 and claims the priority of International Patent Application No. PCT/US2006/040868 filed on Oct. 18, 2006, which in turn claims priority of U.S. Provisional Application No. 60/727,691 filed on Oct. 18, 2005.

BACKGROUND OF THE INVENTION

1. Field of the Invention

The present invention relates to the field of metabolic compound conjugates and variant metabolic compounds, and uses of these in the treatment of diabetes and conditions related to this condition.

2. Description of Related Art

Type 2 diabetes is the most common form of diabetes. In type 2 diabetes, either the body does not produce enough insulin or the cells ignore the insulin. Insulin is necessary for the body to be able to use sugar. Sugar is the basic fuel for the cells in the body, and insulin takes the sugar from the blood into the cells. When glucose builds up in the blood instead of going into cells, it can cause two problems: cells may be starved for energy and high blood glucose levels may damage eyes, kidneys, nerves or heart.

Currently in the United States, 13 million individuals have a diagnosis of diabetes, an estimated 5 million more are suffering from undiagnosed diabetes, and the numbers continue to grow. Approximately 10% of those afflicted have type 1 diabetes, while the rest have type 2. The morbidity and mortality associated with diabetes are related to the short- and long-term complications. Complications include hypoglycemia and hyperglycemia, increased risk of infections, microvascular complications (e.g., retinopathy, nephropathy), neuropathic complications, and macrovascular disease. Diabetes is the major cause of blindness in adults aged 20-74 years, as well as the leading cause of nontraumatic lower-extremity amputation and end-stage renal disease (ESRD).

The first treatment for type 2 diabetes is often meal planning for blood glucose (sugar) control, weight loss, and exercising. Sometimes these measures are not enough to bring blood glucose levels down near the normal range. The next step is taking a medicine that lowers blood glucose levels. In individuals with diabetes, blood glucose levels are too high. These high levels occur because glucose remains in the blood rather than entering cells, where it is utilized. But for glucose to pass into a cell insulin must be present and the cell must be "hungry" for glucose. Individuals with type 1 diabetes don't make insulin. For them, insulin shots are the only way to keep blood glucose levels down. Individuals with type 2 diabetes tend to have two problems: they don't make quite enough insulin and the cells of their bodies don't seem to take in glucose as eagerly as they should.

Metabolic peptides have been used in the treatment of many diseases. For example, glucagon-like peptide (GLP-1) was first identified in the early 1980's and exists in two major forms, GLP-1 (7-36) amide (FIG. 1) and GLP-1 (7-37) (FIG. 2). Both peptides have been shown to be equipotent, but the main peptide in circulation is the GLP-1 (7-36) amide. GLP-1 is processed from the proglucagon gene in the L-cells of the small intestines and has several therapeutic properties. The most desirable antidiabetic action of GLP-1 is its glucose dependent secretion of insulin. Upon the intake of nutrients, GLP-1 is stimulated by the increase in plasma glucose levels and acts at the pancreas to stimulate the production of insulin. Thus, GLP-1 is glucose dependent and only stimulates insulin release as long as there is enough glucose to warrant it. By contrast, most conventional treatments for type 2 diabetes involve insulin secretion that is glucose independent. The properties of GLP-1 make it a suitable candidate for the treatment of non-insulin-dependent diabetes mellitus and type 2 diabetes.

The limitation of GLP-1 as a therapeutic treatment is due to its short in vivo half life (<2 minutes). GLP-1 is degraded rapidly by dipeptidyl peptidase IV (DPP-IV) which cleaves GLP-1 between the 8-9 positions and renders it biologically inactive. In order for GLP-1 to be an effective therapeutic agent, the in vivo half life must be extended and GLP-1 protected from DPP-IV degradation.

A peptide resembling GLP-1 known as exendin-4 is found in the saliva of the Gila monster, a poisonous lizard that lives in the Southwestern United States. The Gila monster eats large, but infrequent, meals. These lizards eat as few as four times each year, storing large amounts of fat in their tails. When the lizard eats, the exendin-4 in the spit of the animal "wakes" the pancreatic islet cells, resulting in beta-cell activity, insulin release, and control of glucose and fat metabolism.

Although exendin-4 was originally found to stimulate amylase secretion from pancreatic acinar cells, subsequent experiments demonstrated that exendin-4 was a potent agonist for the mammalian GLP-1 receptor, consistent with the ~53% amino acid identity that exendin-4 shares with GLP-1. The available evidence suggests that exendin-4 exerts the majority of its glucose-lowering effects through the GLP-1 receptor. Exendin-4 displays similar functional properties to native GLP-1, and regulates gastric emptying, insulin secretion, food intake, and glucagon secretion. Exendin-4 lowers blood glucose in normal rodents and in both mice and rats with experimental diabetes, as reviewed in regulatory peptides (Barragan, Rodriguez et al. 1996).

Exenatide is a synthetic version of exendin-4. It is DPP-IV resistant and has many of the actions of GLP-1. That is, it slows stomach emptying, increases satiety and decreases food intake, and leads to increased release and synthesis of insulin. Exenatide was approved by the FDA in April 2005 for treatment of type 2 diabetes.

Notably, there are practical limitations that exist in using peptides as drugs. Proteolysis, both in the gut and in the bloodstream, is a major barrier to using peptides as therapeutics. Another difficulty encountered with non-endogenous peptides is immunogenicity. The peptides that have been used as therapeutics have generally been limited to administration by repeated subcutaneous injections or by continuous intravenous infusion. As a result of these problems, the approach of the pharmaceutical industry has been to create small, non-peptide molecules using medicinal chemistry. While this approach has met with some success, it is costly, time consuming, and fraught with uncertainty in terms of pharmacokinetics and toxicity. Furthermore, identification of small organic molecules with agonist activity at peptide receptors has proved exceptionally challenging.

Thus is would be advantageous to provide for peptidic conjugate drugs that may be administered and preferably orally administered that exhibit reduce immunogenicity while increasing effectiveness and bioavailability.

SUMMARY OF THE INVENTION

The present invention relates to a pharmacologically active metabolic agent that may be used in a formulation for the treatment of diabetes and conditions related to this condition. The formulations are suitable for oral, nasal, pulmonary, buccal, intravenous, or subcutaneous administration.

In one aspect, the present invention provides for methods of preparing the metabolic compound conjugates, compounds, and formulations containing them, as well as methods of using these conjugates and compounds.

In another aspect, the present invention provides for metabolic compound conjugates comprising:

a metabolic peptide comprising a glucagon-like peptide (GLP-1) receptor binding motif and having at least one oligomer conjugation site; and at least one oligomer attached to the oligomer conjugation site(s).

In one embodiment, the metabolic peptide comprising a glucagon-like peptide (GLP-1) receptor binding motif includes but is not limited to as GLP-1, isolated exendin-3, isolated exendin-4, synthetic exendin-4 or exendin-3, exenatide, functional fragments, analogs or derivatives thereof.

In another embodiment, the metabolic compound conjugates have retained pharmacological activity of the native metabolic peptide, and have enhanced characteristics, such as improved bioavailability, enhanced resistance to proteolytic activity, and/or prolonged activity in the blood stream.

Conjugates according to embodiments of the present invention can be orally administered. Such orally administrable conjugates may provide a more patient-friendly option (and thus superior compliance by the patient) compared to conventional therapies, which require injections.

In other embodiments, the metabolic compound conjugates are provided as hydrolyzable prodrugs, which may have reduced pharmacological activity in the prodrug form relative to the native metabolic peptide, and upon hydrolysis of the prodrug in vivo, an active metabolic compound, is released.

Embodiments of the present invention provide metabolic peptides conjugated to polymeric moieties or oligomers, to provide conjugates that are preferably amphiphilic constructs.

Conjugates according to embodiments of the invention preferably possess improved pharmacokinetic profiles relative to the corresponding unconjugated peptides and are preferably orally administrable. Conjugates according to embodiments of the invention are useful for treating diabetes, especially Type 2 diabetes.

Conjugates according to the present invention may be used in the manufacture of a medicament for the treatment of diabetes or obesity.

The composition of this invention can be administered to a human, or other animal, orally, by injection, implantation (e.g., subcutaneously, intramuscularly, intraperitoneally, intracranially, and intradermally), administration to mucosal membranes (e.g., intranasally, intravaginally, intrapulmonary or by means of a suppository), or in situ delivery (e.g., by enema or aerosol spray). The composition is administered in a therapeutically effective amount to treat a patient suffering from diabetes mellitus, impaired glucose tolerance (IGT), obesity or any other disorder that can be treated by one of the above polypeptides, derivatives or analogs thereof. Other therapeutic properties of the compositions include: suppression of glucagon secretion, slowing of gastric emptying, inhibition of food intake, modulation of glucose trafficking in peripheral tissue, and enhancement of β cell mass (neogenesis, proliferation, suppression of apoptosis).

The use of a polymer moiety or oligomer conjugated to the metabolic peptide improves the bioavailability of the incorporated metabolically active polypeptide and minimizes loss of activity due to instability and/or chemical interactions between the polypeptide and other components contained or used in formulating the sustained release composition, while maintaining an excellent release profile.

DETAILED DESCRIPTION OF EMBODIMENTS OF THE PRESENT INVENTION

Figure 1:
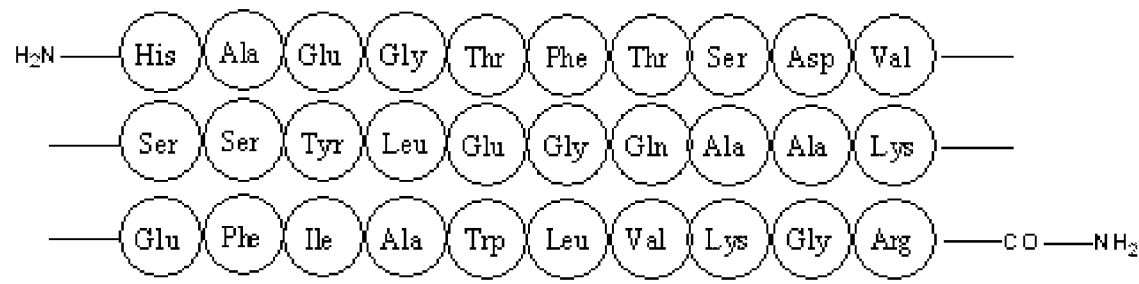
FIG. 1 shows the sequence for GLP-1 (7-36) amide (SEQ ID NO: 1).
Figure 2:
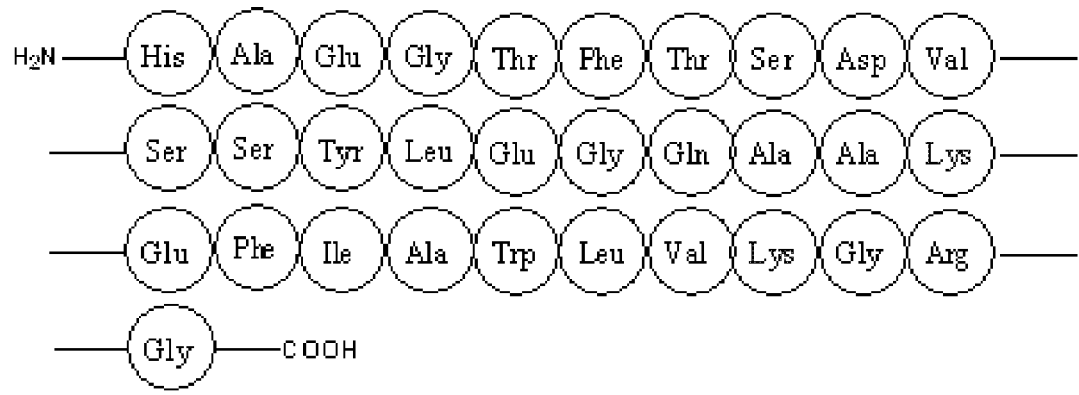
FIG. 2 shows the sequence for GLP-1 (7-37) (SEQ ID NO: 2).
Figure 3:
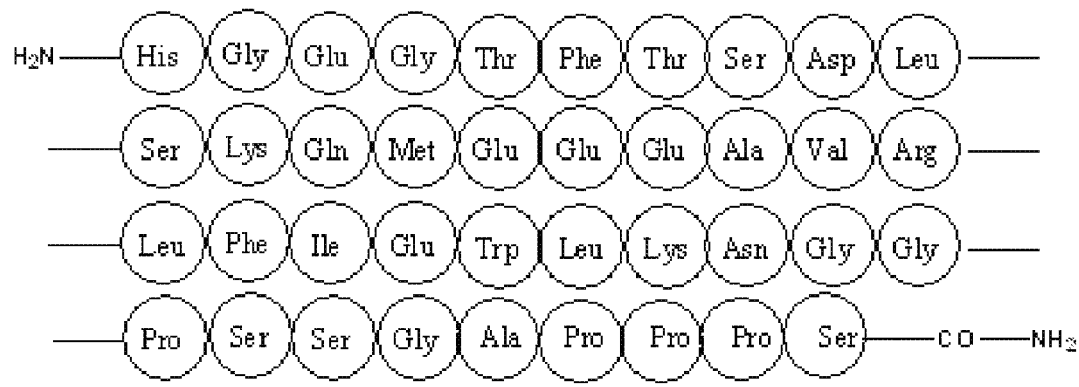
FIG. 3 shows the sequence for Exendin-4 (a 39 amino acid peptide sequence) (SEQ ID NO: 3).
Figure 4:
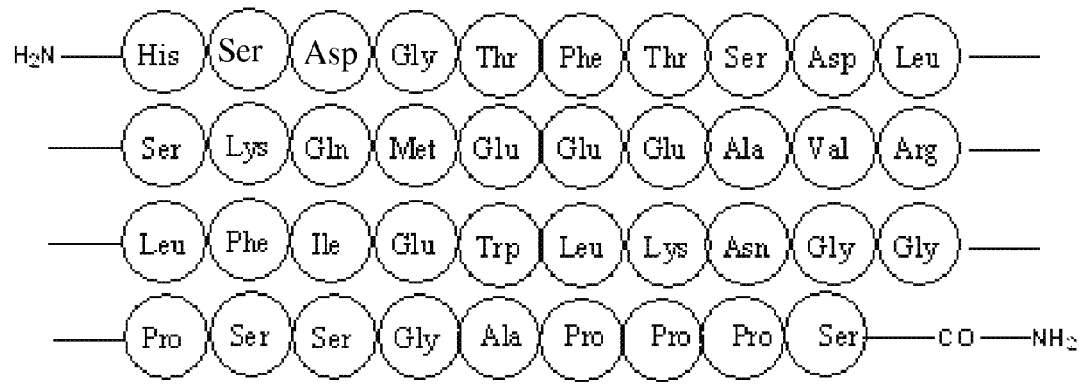
FIG. 4 shows the sequence for Exendin-3 (a 39 amino acid peptide sequence differing at residues 2 and 3) which are approximately 53% homologous to GLP-1) (SEQ ID NO: 4).

The following are definitions of the terms as used throughout this specification and claims. The definitions provided apply throughout the present specification unless otherwise indicated. Terms not defined herein have the meaning commonly understood in the art to which the term pertains.

"Addition," when used in reference to an amino acid sequence, includes extensions of one or more amino acids at either or both ends of the sequence as well as insertions within the sequence.

"Conservative" used in reference to an addition, deletion or substitution of an amino acid means an addition, deletion or substitution in an amino acid chain that does not completely diminish the therapeutic efficacy of the insulin compound, i.e., the efficacy may be reduced, the same, or enhanced, relative to the therapeutic efficacy of scientifically acceptable control, such as a corresponding native insulin compound.

"Hydrophilic" means exhibiting characteristics of water solubility, and the term "hydrophilic moiety" refers to a moiety which is hydrophilic and/or which when attached to another chemical entity, increases the hydrophilicity of such chemical entity. Examples include, but are not limited to, sugars and polyalkylene moieties such as polyethylene glycol.

"Lipophilic" means exhibiting characteristics of fat solubility, such as accumulation in fat and fatty tissues, the ability to dissolve in lipids and/or the ability to penetrate, interact with and/or traverse biological membranes, and the term, "lipophilic moiety" means a moiety which is lipophilic and/or which, when attached to another chemical entity, increases the lipophilicity of such chemical entity.

"Amphiphilic" means exhibiting characteristics of hydrophilicity and lipophilicity, and the term "amphiphilic moiety" means a moiety which is amphiphilic and/or which, when attached to a polypeptide or non-polypeptide drug, increases the amphiphilicity (i.e., increases both the hydrophilicity and the amphiphilicity) of the resulting conjugate, e.g., certain PEG-fatty acid modifying moieties, and sugar-fatty acid modifying moieties.

"Monodispersed" describes a mixture of compounds where about 100 percent of the compounds in the mixture have the same molecular weight. "Substantially monodispersed" describes a mixture of compounds where at least about 95 percent of the compounds in the mixture have the same molecular weight. "Purely monodispersed" describes a mixture of compounds where about 100 percent of the compounds in the mixture have the same molecular weight and have the same molecular structure. Thus, a purely monodispersed mixture is a monodispersed mixture, but a monodispersed mixture is not necessarily a purely monodispersed mixture. "Substantially purely monodispersed" describes a mixture of compounds where at least about 95 percent of the compounds in the mixture have the same molecular weight and same molecular structure. Thus, a substantially purely monodispersed mixture is a substantially monodispersed mixture, but a substantially monodispersed mixture is not necessarily a substantially purely monodispersed mixture. The insulin compound conjugate components of the cation-insulin compound conjugate compositions are preferably monodispersed, substantially monodispersed, purely monodispersed or substantially purely monodispersed, but may also be polydispersed. "Polydispersed" means having a dispersity that is not monodispersed, substantially monodispersed, purely monodispersed or substantially purely monodispersed.

"Substitution" means replacement of one or more amino acid residues within the peptide sequence with another amino acid. In some cases, the substituted amino acid acts as a functional equivalent, resulting in a silent alteration. Substitutions may be conservative; for example, conservative substitutions may be selected from other members of the class to which the substituted amino acid belongs. Examples of nonpolar (hydrophobic) amino acids include alanine, leucine, isoleucine, valine, proline, phenylalanine, tryptophan and methionine. Examples of polar neutral amino acids include glycine, serine, threonine, cysteine, tyrosine, asparagine, and glutamine. Examples of positively charged (basic) amino acids include arginine, lysine and histidine. Examples of negatively charged (acidic) amino acids include aspartic acid and glutamic acid.

The term "GLP-1 agonist", as used herein refers to a molecule, preferably GLP-1 or an analogue or a derivative thereof, or exendin or an analogue or a derivative thereof, or a non-peptidyl compound, which interacts with the GLP-1 receptor and induces the physiological and pharmacological characteristics of the GLP-1 receptor. A GLP-1 agonist binds to the GLP-1 receptor with an affinity constant $K_D$, below 1 µM, preferably below 100 nM. Methods for identifying GLP-1 agonists are well known to those skilled in the art.

Throughout this document, the term "GLP-1 agonist" is also intended to comprise active metabolites and prodrugs thereof, such as active metabolites and prodrugs of GLP-1 or an analogue or a derivative thereof, or exendin or an analogue or a derivative thereof, or a non-peptidyl compound. A "metabolite" is an active derivative of a GLP-1 agonist produced when the GLP-1 agonist is metabolized. A "prodrug" is a compound which is either metabolized to a GLP-1 agonist or is metabolized to the same metabolite(s) as a GLP-1 agonist.

Throughout this document both GLP-1 (7-36) amide (SEQ ID NO: 1) and GLP-1 (7-37) (SEQ ID NO: 2) will simply be referred to as GLP-1. The present invention includes peptides which are derivable from GLP-1. A peptide is said to be "derivable from a naturally occurring amino acid sequence" if it can be obtained by fragmenting a naturally occurring sequence, or if it can be synthesized, based upon a knowledge of the sequence of the naturally occurring amino acid sequence or of the genetic material (DNA or RNA) which encodes this sequence.

Included within the scope of the present invention are those molecules which are said to be analogs or derivatives of GLP-1. Such a "derivative" has the following characteristics: (1) it shares substantial homology with GLP-1 or a similarly sized fragment of GLP-1 and (2) it is capable of functioning as an insulinotropic hormone. A derivative of GLP-1 is said to share "substantial homology" with GLP-1 if the amino acid sequences of the derivative is at least 80%, and more preferably at least 90%, and most preferably at least 95%, the same as that of GLP-1.

An analog is a polypeptide exhibiting some, all or enhanced activity relative to a corresponding native GLP-1 or corresponding to exendins or exenatide or which is converted in vivo or in vitro into a polypeptide exhibiting some, all or enhanced activity relative to a corresponding native GLP-1 or corresponding to exenatide, e.g., a polypeptide having the structure of a human GLP-1 with one or more conservative amino acid additions, deletions and/or substitutions or a polypeptide having the structure of exendins or exenatide with one or more conservative amino acid additions, deletions and/or substitutions.

The derivatives and analogs of the present invention include GLP-1 fragments which, in addition to containing a sequence that is substantially homologous to that of a naturally occurring GLP-1 peptide may contain one or more additional amino acids at their amino and/or their carboxy termini. Thus, the invention pertains to polypeptide fragments of GLP-1 that may contain one or more amino acids that may not be present in a naturally occurring GLP-1 sequence such as a chain of Lys at the N-terminal.

The invention also includes GLP-1 fragments which, although containing a sequence that is substantially homologous to that of a naturally occurring GLP-1 peptide may lack one or more additional amino acids at their amino and/or their carboxy termini that are naturally found on a GLP-1 peptide. Thus, the invention pertains to polypeptide fragments of GLP-1 that may lack one or more amino acids that are normally present in a naturally occurring GLP-1 sequence provided that such polypeptides have an insulinotropic activity comparable to that of GLP-1.

The invention also encompasses the obvious or trivial variants of the above-described fragments which have inconsequential amino acid substitutions (and thus have amino acid sequences which differ from that of the natural sequence) provided that such variants have an insulinotropic activity which is substantially identical to that of the above-described GLP-1 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Exendin-4 and exendin-3, are naturally-occurring hormones that were first isolated from the saliva of the Gila monster and Heloderma lizards, respectively. Exendin-4 is much more potent than native GLP-1, largely due to its improved PK profile as a result of resistance to DPP-IV-mediated inactivation. In contrast to GLP-1 which contains an alanine at position 2, exendin-4 has a glycine at position 2, hence it is not a substrate for DPP IV and has a much longer half-life in vivo. The potent glucose-lowering properties of exendin-4, taken together with its comparatively prolonged duration of action, prompted studies employing exendin-4 for the treatment of patients with Type 2 diabetes. Exendin-4 has a longer half-life than GLP-1 and has very recently been shown to have a hypoglycemic effect in humans when given twice a day for one month. Like glucagon and glucagon-like-peptide 1, exendin-4 increases insulin release only following meals.

Exendin-4 has been administered acutely or for several weeks to mice and rats with experimental diabetes, producing improved glucose control, reduced hemoglobin A1C, increased insulin, weight loss, decreased adiposity, reduced food intake, and stimulation of islet neogenesis and islet proliferation.

Exendin 3 and Exendin 4 are 39 amino acid peptides (differing at residues 2 and 3) which are approximately 53% homologous to GLP-1 and find use as insulinotropic agents. The Exendin-3 (SEQ ID No: 3) sequence is HSDGTFTSDL-SKQMEEEAVRLFIEWLKNGGPSSGAPPPS and the Exendin-4 (SEQ ID No: 4) sequence is HGEGTFTSDL-SKQMEEEAVRLFIEWLKNGGPSSGAPPPS.

The present invention includes peptides which are derivable from the naturally occurring exendin 3 and exendin 4 peptides. A peptide is said to be "derivable from a naturally occurring amino acid sequence" if it can be obtained by fragmenting a naturally occurring sequence, or if it can be synthesized, based upon a knowledge of the sequence of the naturally occurring amino acid sequence or of the genetic material (DNA or RNA) which encodes this sequence.

Included within the scope of the present invention are those molecules which are said to be analogs or derivatives of exendin 3 and exendin 4 and having the same meaning as set forth above. A derivative or analog of exendin 3 and exendin 4 is said to share "substantial homology" with exendin 3 and exendin 4 if the amino acid sequences of the derivative is at least 80%, and more preferably at least 90%, and most preferably at least 95%, the same as that of either exendin 3 or 4 or a fragment of exendin 3 or 4.

The derivatives of the present invention include exendin-3 or exendin-4 fragments which, in addition to containing a sequence that is substantially homologous to that of a naturally occurring exendin-3 or exendin-4 peptide may contain one or more additional amino acids at their amino and/or their carboxy termini. Thus, the invention pertains to polypeptide fragments of exendin-3 or exendin-4 that may contain one or more amino acids that may not be present in a naturally occurring exendin-3 or exendin-4 sequences provided that such polypeptides have an insulinotropic activity comparable to that of exendin-3 or exendin-4.

Similarly, the invention includes exendin-3 or exendin-4 fragments which, although containing a sequence that is substantially homologous to that of a naturally occurring exendin-3 or exendin-4 peptide may lack one or more additional amino acids at their amino and/or their carboxy termini that are naturally found on a exendin-3 or exendin-4 peptide. Thus, the invention pertains to polypeptide fragments of exendin-3 or exendin-4 that may lack one or more amino acids that are normally present in a naturally occurring exendin-3 or exendin-4 sequence provided that such polypeptides have an insulinotropic activity which is comparable to that of exendin-3 or exendin-4.

The invention also encompasses the obvious or trivial variants of the above-described fragments which have inconsequential amino acid substitutions (and thus have amino acid sequences which differ from that of the natural sequence) provided that such variants have an insulinotropic activity which is substantially comparable to that of the above-described exendin-3 or exendin-4 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Exenatide (brand name Byetta®) is the first in a new class of drugs for the treatment of type 2 diabetes called incretin mimetics. Exenatide is a 39 amino acid sequence and is a synthetic version of exendin-4 which works to lower blood glucose levels primarily by increasing insulin secretion. The amino acid sequence of exendin-4 can be found in U.S. Pat. No. 5,424,286 issued to Eng on Jun. 13, 1995, the entire content of which is hereby incorporated by reference. Exendin-4 has been shown in humans and animals to stimulate secretion of insulin in the presence of elevated blood glucose concentrations, but not during periods of low blood glucose concentrations (hypoglycemia). It has also been shown to suppress glucagon secretion, slow gastric emptying and affect food intake and body weight, as well as other actions. As such, exendin-4 and analogs and agonists thereof can be useful in the treatment of diabetes mellitus, IGT, obesity, etc.

In one aspect, embodiments of the present invention target the GLP-1 receptor with a conjugate of a metabolic peptide comprising a glucagon-like peptide (GLP-1) receptor binding motif, such as exenatide or GLP-1, to initiate production of cAMP. The polymeric moiety or oligomer used to conjugate the exenatide or GLP-1 may, for example, include PEG moieties and/or alkyl groups. The hydrophobicity and hydrophilicity of drug molecules can be varied by varying the lengths of the PEG moieties and/or alkyl groups. In one embodiment, the invention provides a non-immunogenic peptide conjugate that has increased resistance to degradative enzymes and is suitable for oral delivery and transport across the intestinal epithelium.

Conjugated exendin-3, exendin-4, exenatide or GLP-1 according to embodiments of the present invention may induce the pancreatic and/or gastric effects that are associated with the native peptide. In preferred embodiments, conjugation will reduce or slow proteolysis and facilitate delivery into the systemic circulation through the gut wall, resulting in glucose-dependent insulin secretion, inhibition of glucagon and gastric acid secretion, and/or delay of gastric emptying.

Conjugated peptide complexes comprising a glucagon-like peptide (GLP-1) receptor binding motif according to embodiments of the present invention that can be delivered orally (instead of by injection) may increase patient compliance, delay the patients' dependence on exogenous insulin, and thus help prevent the weight gain that often occurs when a patient begins insulin therapy.

According to embodiments of the present invention a metabolically active peptide, exendin-3, exendin-4, exenatide (an exogenous 39 amino acid peptide) or GLP-1 (an endogenous 30-31 amino acid peptide) is conjugated to a polymer or oligomer. The polymer or oligomer may be amphiphilic and/or provides an amphiphilic conjugate upon conjugation. As used herein, the term "amphiphilic" means the ability to dissolve in both water and lipids, and the term "amphiphilic oligomer" and "amphiphilic polymer" mean a moiety which is amphiphilic and/or which, when attached to a polypeptide, increases the amphiphilicity of the resulting conjugate.

According to some embodiments of the present invention, the polymeric or oligomeric moiety used to conjugate the peptides will be amphiphilic oligomers having a polyethylene glycol moiety (PEG), which is hydrophilic, and an alkyl moiety, which is lipophilic. When conjugated to peptides, these amphiphilic oligomers increase the solubility of the peptide in both aqueous and non-aqueous environments. The result is a peptide conjugate that is better suited for oral administration and epithelial penetration than is the native peptide. The oligomers also preferably provide a physical barrier to the degradative enzymes of the digestive tract and systemic circulation. In short, the oligomers offer increased solubility in the aqueous environment of the body, increased absorption through the intestinal epithelial cell layer, and/or increased resistance to enzymatic degradation.

The polymer or oligomer may be or include an alkyl moiety, e.g., an alkyl having from 1 to 25 carbons. The polymer or oligomer may be or include a lipophilic moiety and/or render the conjugate more lipophilic with the polymer or oligomer than without. The polymer or oligomer may be hydrophilic and/or render the conjugate more lipophilic with the polymer or oligomer than without. The polymer or oligomer may be or include a polyalkalene glycol moiety. The polymer or oligomer may include linear, branched or cyclic components.

While much of the description of the invention focuses on exendin-4, exendin-3, exenatide and GLP-1 peptides, it is to be understood that analogs, fragments, and/or fragment analogs that retain some or all of the activity of the native peptides may be useful in embodiments of the present invention. Such analogs, fragments, or fragment analogs may be provided by various methods as will be understood by those skilled in the art, such as the methods described in U.S. patent application Ser. No. 09/873,797, filed Jun. 4, 2001, the entire disclosure of which is incorporated herein by reference.

The conjugates of the invention can be tested for agonist activity at the human GLP-1 receptor in vitro. The metabolic properties of exenatide and GLP-1 are ascribed to a secondary messenger, cyclic AMP (cAMP). The production of cAMP is accomplished by activation of a G-protein-coupled receptor. cAMP production can be measured in cell cultures that naturally express the receptor. Thus, the relative activity of the exendin-3, exendin-4, exenatide or GLP-1 conjugates can be determined by the level of cAMP production by these cells.

The conjugates of the invention can be tested for increased resistance to proteases. In general, drugs that are delivered orally are subjected to digestive enzymes such as pepsin, trypsin, and/or chymotrypsin. In the case of peptide drugs, these enzymes may be particularly problematic. However, peptide conjugation according to the present invention, an increased resistance to these enzymes. Digestive enzyme cocktails can be used to test for increased resistance of the conjugates of the invention to proteases of the digestive tract. They can also be tested for stability in the presence of DPP-IV, a protease that is a primary means of removal of active GLP-1 from systemic circulation.

According to embodiments of the present invention, conjugates of exendin-3, exendin-4, exenatide or GLP-1 can activate the GLP-1 receptor and trigger production of cAMP. Conjugated peptides may, for example, be protected from proteolytic degradation, i.e., the conjugate is degraded more slowly than the corresponding unconjugated compound.

Conjugates according to embodiments of the present invention may preferably be orally and/or perorally available, i.e., a therapeutically significant amount of the conjugate can be delivered by the oral and/or peroral routes. The conjugated peptide may retain some or all of the activity of native peptide with the additional benefits of oral administration. Such a compound may increase patient compliance and/or delay the need for administration of exogenous insulin.

The pharmaceutical characteristics, such as hydrophilicity and/or lipophilicity of the conjugates according to embodiments of the present invention can be varied by adjusting the number of PEG monomers, the type and length of alkyl chain, the nature of the PEG-peptide linkage, the sites of conjugation and the number of conjugation sites. The exact nature of the PEG-peptide linkage can be varied such that it is stable and/or sensitive to hydrolysis at physiological pH or in plasma.

Cell-based assays may be used to show which conjugates are proficient agonists of the GLP-1 receptor, leading to the suitable production of cAMP. Biochemical assays may be used to show which conjugates offer the suitable protection against proteolytic enzymes. In vivo experiments may be used to show which conjugates afford a desirable efficacy after oral administration. Leading conjugates can be tested in established dog models. Desirable candidates may be subjected to detailed pharmacokinetic, pharmacodynamic, and toxicity studies in rats and/or dogs. Exenatide or GLP-1 conjugates according to embodiments of the present invention are useful for the chronic treatment of patients with varying degrees of Type 2 diabetes.

Exenatide, a synthetic version of exendin-4, may be modified with polymers or oligomers (used interchangeably herein), for example, include polyethylene glycol moiety (PEG), which is hydrophilic, and/or an alkyl moiety, which is lipophilic. When conjugated to peptides, these oligomers increase the solubility of the peptide in both aqueous and non-aqueous environments. The result is a peptide conjugate that is better suited for oral administration and epithelial penetration than is the native peptide. The oligomers also provide a physical barrier to the degradative enzymes of the digestive tract. In short, the oligomers offer increased solubility in the aqueous environment of the body, increased absorption through the intestinal epithelial cell layer, and increased resistance to enzymatic degradation. Conjugating to exenatide with oligomers (modifying moieties), may be used to improve the pharmacokinetic profile of exenatide and facilitate its oral delivery. Preferred oligomers are well tolerated and non-toxic. In one embodiment the conjugates will contain no modified or unnatural amino acids. However, the peptide may include modified or unnatural amino acids. The peptide may include all D amino acids, all L amino acids, or a mixture of both.

Preferred conjugates have reduced proteolysis, immunogenicity, and altered hydrophilicity and hydrophobicity. While the use of pegylated proteins is well established, they had previously been confined to injectable use. Preferred oligomers include short, defined PEG units linked to alkyl chains. By adjusting the number of PEG monomers, the type and length of alkyl chain, and the nature of the PEG-peptide linkage, desired properties of hydrophilicity/hydrophobicity can be designed for the specific indication. In addition, the exact nature of the PEG-peptide linkage can be varied such that it is stable or sensitive to hydrolysis at physiological pH or in plasma. Such variations are understood by those of ordinary skill in the art, and are within the scope of the invention.

The conjugates of the invention can have a different level of biological activity relative to the corresponding unconjugated exenatide compound or GLP-1 compound. In some embodiments, the conjugate retains some or all of the activity of the unmodified parent, but by virtue of factors such as the degree of conjugation with modifying moieties, selection of conjugation sites on the molecule and selection of modifying moieties, is less susceptible to in vivo degradation, and thus, has an increased plasma half life. For example, the compounds of the invention may be modified to include an oligomer at one, two, three, four, five, or more sites on the parent compound structure at appropriate attachment (i.e., oligomer conjugation) sites suitable for facilitating the association of an oligomer thereon. By way of example, such suitable conjugation sites may comprise an amino acid residue, such as a lysine amino acid residue.

In many embodiments, for example, the metabolically active agent functions, in part, by binding to an active site in a receptor. Often, when a functional group, such as an amino acid residue is modified, the agent no longer binds in the active site. However, in the case of exenatide, for example, the peptide has a particular affinity for binding to the GLP-1 receptor. Depending on the site at which the exenatide molecule is modified to include the modifying group, the activity that the exenatide has at the receptor may be the same, or may be reduced (measured by reference to the $E_{max}$ of the exenatide compound conjugates). In some embodiments, the exenatide compound conjugates have less activity than has native, unconjugated exenatide, but display improved characteristics relative to unconjugated exenatide, such as increased resistance to proteolysis and plasma half-life or ability to cross a cell membrane. Reduced activity may in some instances be preferred, for example, when long term release of the compound is desirable.

In some embodiments, the conjugates are monoconjugates. In other embodiments, the conjugates are multi-conjugates, such as di-conjugates, tri-conjugates, tetra-conjugates, penta-conjugates and the like. The number of modifying moieties on the parent compound is limited only by the number of conjugation sites on the parent compound. In still other embodiments, the conjugates of the present invention are a mixture of mono-, di-, and/or tri-oligomer conjugates.

For example, in some embodiments, the biologically active compound is exenatide, which has within the sequence of its 39 native amino acid residues with three preferred conjugation sites, including the N-terminus, $Lys^{12}$, and $Lys^{27}$. In some embodiments, the invention provides exenatide compound monoconjugates conjugated at the N-terminus, $Lys^{12}$, or $Lys^{27}$, or di-conjugates at N-terminus/$Lys^{12}$, $Lys^{12}$/$Lys^{27}$ or N-terminus/$Lys^{27}$.

In other embodiments, the biologically active compound is GLP-1, which has within the sequence of its 30 or 31 (SEQ ID NO: 1 or SEQ ID NO: 2) native amino acid residues has, three preferred conjugation sites, including the N-terminus, $Lys^{20}$, and $Lys^{28}$. In some embodiments, the invention provides GLP-1 compound monoconjugates conjugated at the N-terminus, $Lys^{20}$, or $Lys^{28}$, or di-conjugates at N-terminus/$Lys^{20}$, $Lys^{20}$/$Lys^{28}$ or N-terminus/$Lys^{28}$.

The oligomer may be covalently coupled to the parent compound. More than one moiety on the oligomer may be covalently coupled to the parent compound. Coupling may employ hydrolyzable or non-hydrolyzable bonds or mixtures of the two (i.e., different bonds at different conjugation sites).

In some embodiments, the compound is coupled to the oligomer utilizing a hydrolyzable bond (e.g., an ester bond). Use of a hydrolyzable coupling will provide a compound conjugate that acts as a prodrug, which is a compound that must undergo chemical conversion by metabolic processes before becoming an active pharmacological agent. A prodrug approach may be desirable where the conjugate is inactive (i.e., the conjugate lacks the ability to affect the body through the compound's primary mechanism of action) or has limited, minimal or reduced activity relative to the parent compound, such as when the oligomer conjugation site is in a binding region of the compound. Use of a hydrolyzable coupling can also provide for a time-release or controlled-release effect, administering the active parent compound over a given time period as one or more modifying moieties are cleaved from their respective conjugates to provide the active drug.

In other embodiments, the parent compound is coupled to the oligomer utilizing a non-hydrolyzable bond (e.g., a carbamate, amide, or ether bond). Use of a non-hydrolyzable bond may be preferable when it is desirable to allow the conjugate to circulate in the bloodstream for an extended period of time, preferably at least 2 hours. Bonds used to covalently couple the compound to the oligomer in a non-hydrolyzable fashion are typically selected from the group consisting of covalent bond(s), ester moieties, carbonate moieties, carbamate moieties, amide moieties and secondary amine moieties.

In still other embodiments, a partial prodrug approach may be used, in which a portion of the oligomer is hydrolyzed. For example, U.S. Pat. No. 6,309,633 describes modifying moieties comprising hydrophilic and lipophilic components in which the lipophilic components hydrolyze in vivo to yield a micropegylated conjugate.

More than one oligomer (i.e., a plurality of modifying moieties) may be coupled to the parent compound. The modifying moieties in the plurality are preferably the same. However, it is to be understood that the modifying moieties in the plurality may be different from one another, or, alternatively, some of the modifying moieties in the plurality may be the same and some may be different. When a plurality of modifying moieties are coupled to the parent compound, it may be preferable to couple one or more of the modifying moieties to the parent compound with hydrolyzable bonds and couple one or more of the modifying moieties to the parent compound with non-hydrolyzable bonds.

Alternatively, all of the bonds coupling the plurality of modifying moieties to the parent compound may be hydrolyzable, but have varying degrees of hydrolyzability such that, for example, one or more of the modifying moieties may be rapidly removed from the parent compound by hydrolysis in the body and one or more of the modifying moieties is slowly removed from the parent compound by hydrolysis in the body.

The oligomer may be coupled to the parent compound at various nucleophilic residues of the drug including, but not limited to, nucleophilic hydroxyl functions and/or amino functions. Nucleophilic hydroxyl functions may be found, for example, at serine and/or tyrosine residues, and nucleophilic amino functions may be found, for example, at histidine and/or Lys residues, and/or at the N-terminus of the polypeptide.

The oligomer may, for example, have a formula:

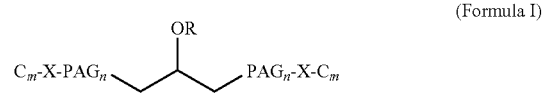
(Formula I)

wherein each C is independently selected and is an alkyl moiety having m carbons and m is a number from 2 to 20, preferably 2 to 15, still more preferably 2 to 10; and each polyalkylene glycol moiety (PAG) is independently selected and is a PAG moiety having n subunits and n is a number from 2 to 25, preferably 2 to 18, more preferably 2 to 16; each X is independently selected and is a linking moiety coupling PAG to C, and is preferably —C—, —O—, —C(O)—, —NH—, —NHC(O)—, or —C(O)NH—, and wherein R is —H, —OH, —C(O)OH or an activating moiety, such as C(O)X' or OC(O)X' (where X' is a halide (e.g., Cl, Br) or p-nitrophenol), or

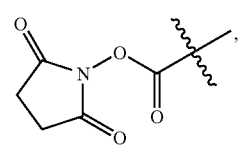 [SMILES: *C(=O)ON1C(=O)CCC1=O]

The oligomer may have a formula:

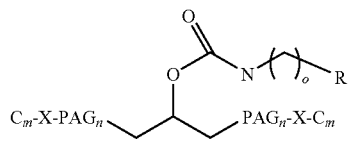

(Formula II)

wherein each C is independently selected and is an alkyl moiety having m carbons and m is a number from 0 to 20, and preferably from 1 to 10; and each PAG is independently selected and is a polyalkylene glycol moiety having n subunits and n is a number from 0 to 25, and preferably from 1 to 15; each X is independently selected and is a linking moiety coupling PAG to C, and is preferably —C—, —O—, —C(O)—, —C(O)O—, —OC(O)—, —NH—, —NHC(O)—, or —C(O)NH—; o is a number from 0 to 15 and preferably from 1 to 10. The $C_m$—X moiety may be absent, and the $PAG_n$ moiety terminated with an —OH moiety or an —OCH$_3$ moiety. For example, the PAG may be methoxy-terminated or hydroxy-terminated PEG, having from 1 to 20 subunits. R may be —H, —OH, —C(O)OH or an activating moiety, such as C(O)X' or OC(O)X' (where X' is a halide (e.g., Cl, Br) or p-nitrophenol), or

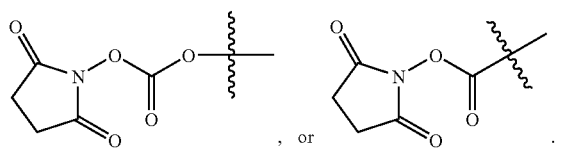 [SMILES: *OC(=O)ON1C(=O)CCC1=O ; *C(=O)ON1C(=O)CCC1=O]

The oligomer may have a formula:

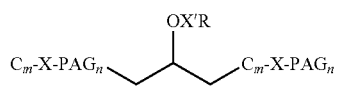

(Formula III)

wherein each C is independently selected and is a saturated or unsaturated alkyl moiety having m carbons and m is a number from 0 to 20, and preferably from 1 to 10; and each PAG is independently selected and is a polyalkylene glycol moiety having n subunits and n is a number from 0 to 25, and preferably from 1 to 15; each X is independently selected and is a linking moiety coupling PAG to C, and is preferably —C—, —O—, —C(O)—, —C(O)O—, —OC(O)—, —NH—, —NHC(O)—, or —C(O)NH—, wherein R is H, C(O)OH or an activating moiety, such as C(O)X" (where X" is a halide (e.g., Cl, Br) or p-nitrophenol), or

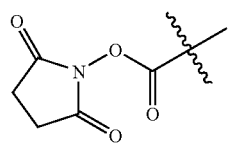

The oligomer may, for example, have a formula:

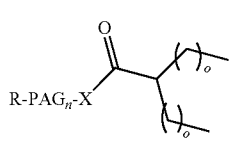

(Formula IV)

wherein each C is independently selected and is an alkyl moiety having m carbons and m is a number from 0 to 20, and preferably from 1 to 10; and each PAG is independently selected and is a polyalkylene glycol moiety having n subunits and n is a number from 0 to 25, and preferably from 1 to 15; X is —O—, or —NH—; each o is independently selected and is a number from 1 to 15, and wherein R is —H, —OH, —C(O)OH or an activating moiety, such as C(O)X' or OC(O)X' (where X' is a halide (e.g., Cl, Br) or p-nitrophenol), or

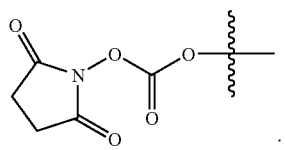 [SMILES: *OC(=O)ON1C(=O)CCC1=O]

The oligomer may, for example, have a formula:

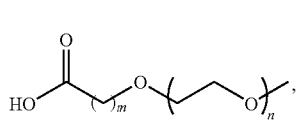

(Formula V)

where m is a number from 0-20, and preferably from 1 to 10, and n is a number from 0-25, and preferably from 1 to 15; and/or

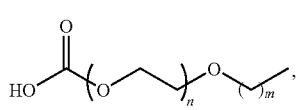

(Formula VI)

where m is a number from 0 to 20, and preferably from 1 to 10, and n is a number from 0 to 25, and preferably from 1 to 15.

The oligomer may, for example, have a formula:

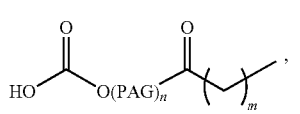

(Formula VII)

where m is a number from 0 to 20, and preferably from 1 to 10; and PAG is a PAG moiety having n subunits and n is a number from 0 to 25, and preferably from 1 to 15.

The pharmaceutical characteristics, such as hydrophilicity/lipophilicity of the conjugates according to embodiments of the present invention can be varied by adjusting the number of PEG monomers, the type and length of alkyl chain, the nature of the PEG-peptide linkage, and the number of conjugation sites. The exact nature of the PEG-peptide linkage can be varied such that it is stable and/or sensitive to hydrolysis at physiological pH or in plasma.

GLP-1 is preferably modified in a way that protects it from DPP-IV degradation (i.e., degradation is reduced relative to the corresponding unconjugated GLP-1 compound). A preferred strategy is conjugation of oligomer(s) to the N-terminus of GLP-1. Conjugation at the N-terminus is suitable for providing resistance to DPP-IV (i.e., to reduce degradation relative to corresponding unconjugated compound). Retaining the activity of GLP-1 is an important issue, as conjugation to the N-terminus can result in loss of biological activity. The loss of activity can be curtailed or the activity retained by a number ways: conjugation of small oligomers at the N-terminus, hydrolyzable oligomers that leave a small PEG unit attached to the N-terminus (micropegylation), and alkylation of the N-terminus which will retain the basic nature of amino function of the N-terminus.

Another novel approach is to attach structures as shown herein directly below:

which have "rigidity" at the β position. This "rigidity" at the β position can be in the form of a double bond, ring system, or a functional group that hinders rotation around that bond. These types of structures when conjugated to GLP-1, and other peptides susceptible to proteolytic cleavage by DPP-IV, have shown resistance to DPP-IV and have retained the activity of the native peptide. In one embodiment, the invention provided modification of these "rigid" hydrophobic structures to increase bioavailability of GLP-1 for oral delivery.

The oligomer may be a straight or branched polymeric moiety comprising one or more straight or branched polyalkylene glycol moieties and/or one or more straight or branched, substituted or unsubstituted alkyl moieties. However, in certain embodiments, the oligomer specifically does not consist of an alkyl moiety and in other embodiments, the oligomer specifically does not consist of an alkane moiety. The polyalkylene glycol moieties in some embodiments include from 1 to 25 polyalkylene glycol subunits, more preferably from 2 to 20, ideally from 2 to 15. The polyalkylene glycol moieties in some embodiments comprise PEG. The alkyl moieties in some embodiments are preferably a number from 2 to 20, more preferably from 2 to 15, more preferably from 2 to 10 carbon atoms. The alkyl moieties are preferably alkane moieties.

The oligomer may, for example, have a formula:

(Formula VIII)

wherein each C is independently selected and is an alkyl moiety having m carbons and m is a number from 1 to 20, preferably 1 to 15, still more preferably 2 to 10; and each PAG is independently selected and is a polyalkylene glycol moiety having n subunits and n is a number from 1 to 25, preferably 2 to 18, more preferably 2 to 16; X is independently selected and is a linking moiety coupling PAG to C, and is preferably —C—, —O—, —C(O)—, —C(O)O—, —NH—, —NHC(O)—, or —C(O)NH—; Z is independently selected and is a linking moiety coupling PAG to amine function, and is preferably —C—, —C(O)—. With respect to Formulas I and II, and in some embodiments the Cm—X moiety is absent, and the PAGn moiety is terminated with an —OH moiety or an —OCH3 moiety. For example, the PAG may be methoxy-terminated or hydroxy-terminated PEG, having 1, 2, 3, 4, 5, 6, 7, 8, 9, 10, 11, 12, 13, 14, 15, 16, 17, 18, 19 or 20 subunits.

The oligomer may, for example, have a formula:

(Formula IX)

wherein each C is independently selected and is an alkyl moiety having m carbons and m is a number from 1 to 20, preferably 2 to 15, still more preferably a number from 2 to 10; and each PAG is independently selected and is a polyalkylene glycol moiety having n subunits and n is a number from 1 to 25, preferably 2 to 18, more preferably 2 to 16; X is independently selected and is a linking moiety coupling PAG to C, and is preferably —C—, —O—, —C(O)—, —C(O)O—, —NH—, —NHC(O)—, or —C(O)NH—; Z is independently selected and is a linking moiety coupling PAG to the alkyl chain, and is preferably —C—, —O—, —C(O)—, —OC(O)—, —NHC(O)—, —C(O)NH—.

With respect to Formulas I and II, and in some embodiments the Cm—X moiety is absent, and the PAGn moiety is terminated with an —OH moiety or an —OCH$_3$ moiety. For example, the PAG may be methoxy-terminated or hydroxy-terminated PEG, having 1, 2, 3, 4, 5, 6, 7, 8, 9, 10, 11, 12, 13, 14, 15, 16, 17, 18, 19 or 20 subunits.

Where the polymer or oligomer is PEG or includes PEG, the PEG may be monodispersed, substantially monodispersed, purely monodispersed or substantially purely monodispersed (e.g., as previously described by the applicants in U.S. patent Ser. No. 09/873,731 and U.S. patent Ser. No. 09/873,797, both filed 4 Jun. 2001, the entire disclosures of which are incorporated herein by reference) or polydispersed.

Where the polymer or oligomer is PEG or includes PEG, the PEG may be branched, which can in one embodiment be represented as R(PEG$_n$OH)m in which R represents a central (typically polyhydric) core agent such as pentaerythritol, sugar, lysine or glycerol, n represents the number of PEG subunits and can vary for each arm and is typically 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 and m represents the number of arms, and ranges from 2 to the maximum number of attachment sites on the core agent. Each branch can be the same or different and can be terminated, for example, with ethers and/or esters. The number of arms m can range from three to a hundred or more, and one or more of the terminal hydroxyl groups can be coupled to the remainder of the parent compound, or otherwise subject to chemical modification.

In some embodiments, the oligomers include one or more lipophilic moieties. The lipophilic moiety may be various lipophilic moieties as will be understood by those skilled in the art including, but not limited to, alkyl moieties, alkenyl moieties, alkynyl moieties, aryl moieties, arylalkyl moieties, alkylaryl moieties, fatty acid moieties, adamantantyl, and cholesteryl, as well as lipophilic polymers and/or oligomers.

Where the polymer or oligomer is an alkyl moiety or includes an alkyl moiety, the alkyl moiety can be a saturated or unsaturated, linear, branched, or cyclic hydrocarbon chain. In some embodiments, the alkyl moiety has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more carbon atoms. Examples include saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec butyl, tert butyl, 2 methylbutyl, tert pentyl, 2 methyl pentyl, 3 methylpentyl, 2 ethylhexyl, 2 propylpentyl; and unsaturated alkyl moieties derived from the above saturated alkyl moieties including, but not limited to, vinyl, allyl, 1 butenyl, 2 butenyl, ethynyl, 1 propynyl, and 2 propynyl. In other embodiments, the alkyl moiety is a lower alkyl moiety. In still other embodiments, the alkyl moiety is a C1 to C3 lower alkyl moiety.

In some embodiments, the oligomer specifically does not consist of an alkyl moiety, or specifically does not consist of a lower alkyl moiety, or specifically does not consist of an alkane moiety, or specifically does not consist of a lower alkane moiety.

The polymer or oligomer may include a lipophilic moiety. The lipophilic moiety may be a fatty acid moiety, such as a natural or synthetic, saturated or unsaturated, linear or branched fatty acid moiety. In some embodiments, the fatty acid moiety has 2, 3, 4, 5, 6, 7, 8, 9, 10, 11, 12, 13, 14, 15, 16, 17, 18, 19, 20, 21, 22, 23, 24, or more carbon atoms.

In some embodiments, the oligomer specifically does not consist of a fatty acid moiety; or specifically does not consist of a fatty acid moiety having 2, 3, 4, 5, 6, 7, 8, 9, 10, 11, 12, 13, 14, 15, 16, 17, 18, 19, 20, 21, 22, 23, 24 or more carbon atoms.

The oligomer may be a linear or branched polymeric moiety having one or more linear or branched PAG moieties and/or one or more linear or branched, substituted or unsubstituted alkyl moieties. In certain cases, such moieties are considered amphiphilic; however, the PAG and alkyl moieties may be varied to render such moieties more lipophilic or more hydrophilic. In certain embodiments, the oligomer specifically does not consist of an alkyl moiety and in other embodiments, the oligomer specifically does not consist of an alkane moiety.

The PAG moieties in some embodiments include 1, 2, 3, 4, 5, 6, 7, 8, 9, 10, 11, 12, 13, 14, 15, 16, 17, 18, 19, 20, 21, 22, 23, 24, or 25 PAG subunits arranged in linear or branched form. The PAG moieties in some embodiments include PEG, PPG and/or PBG subunits. The alkyl moieties in some embodiments preferably have 2, 3, 4, 5, 6, 7, 8, 9, 10, 11, 12, 13, 14, 15, 16, 17, 18, 19, or 20 carbon atoms. The alkyl moieties are preferably alkane moieties. The oligomer may include a capping moiety, such as —OCH$_3$. Further, the oligomer may include a hydrophobic group, such as a pivaloyl group.

In a related embodiment, the oligomer has a formula:

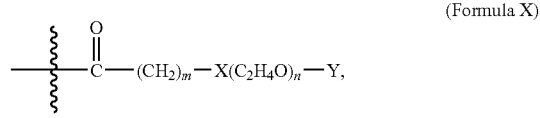

(Formula X)

where m is 1, 2, 3, 4, 5, 6, 7, 8, 9, 10, 11, 12, 13, 14, 15, 16, 17, 18, 19, 20, 21, 22, 23, 24, or 25 and n is a number from 2 to 100, preferably 2 to 50, more preferably 2, 3, 4, 5, 6, 7, 8, 9, 10, 11, 12, 13, 14, 15, 16, 17, 18, 19, 20, 21, 22, 23, 24 or 25, X is —C—, —O—, —C(O)—, —NH—, —NHC(O)—, or —C(O)NH—, and Y is lower alkyl or —H. X is preferably O and Y is preferably —CH$_3$. In some cases, the carbonyl group (—C(O)—) may be absent, and the —(CH$_2$)— moiety may be coupled to an available group on an amino acid, such as a hydroxyl group or a free carboxylic acid group.

In a preferred embodiment, the oligomer has a structure selected from the following:

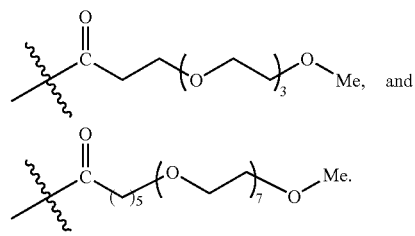

Any of the foregoing moieties may, for example, be coupled to human GLP-1 at a nucleophilic residue. In some cases, the carbonyl group (—C(O)—) may be absent or replaced with an alkyl moiety, preferably a lower alkyl moiety, and the —(CH$_2$)— moiety may be coupled to an available group on an amino acid, such as a hydroxyl group or a free carboxylic acid group.

In another embodiment, the oligomer may have a formula:

(Formula VI)

wherein,
X, Y and Z are independently selected linking groups and each is optionally present, and X, when present, is coupled to the parent compound by a covalent bond,
at least one of R$^1$ and R$^2$ is present, and is lower alkyl and may optionally include a carbonyl group, R$^2$, if present, is a capping group, such as —CH$_3$, —H, tosylate, or an activating group, and
PAG is a linear or branched carbon chain incorporating one or more alkalene glycol moieties (i.e., oxyalkalene moieties), and optionally incorporating one or more additional moieties selected from the group consisting of —S—, —O—, —N—, and —C(O)—, and
wherein the oligomer has a maximum number of 3, 4, 5, 6, 7, 8, 9, 10, 11, 12, 13, 14, 15, 16, 17, 18, 19, 20, 21, 22, 23, 24, or 25 heavy atoms.

In embodiments of the invention, any one or more of X, Y and Z may be absent. Further, when present, X, Y and/or Z may be independently selected from —C(O)—, —O—, —S—, —C— and —N—.

In one embodiment, Z is —C(O)—. In another embodiment, Z is not present.

In some embodiments, $R^1$ is lower alkyl, and $R^2$ is not present. In other embodiments, $R^2$ is lower alkyl, and $R^1$ is not present.

In another embodiment, the oligomer may include a linear or branched, substituted carbon chain moiety having a backbone of 3, 4, 5, 6, 7, 8, 9, 10, 11, 12, 13, 14, 15, 16, 17, 18, 19, 20, 21, 22, 23, 24 or 25 atoms selected from the group consisting of —C, —C—, —O—, =O, —S—, —N—, and —Si—. The heavy atoms will typically include one or more carbon atoms and one or more non-carbon heavy atoms selected from the group consisting of —O—, —S—, —N—, and =O.

The carbon atoms and non-carbon heavy atoms are typically present in a ratio of at least 1 carbon atom for every non-carbon heavy atom, preferably at least 2 carbon atoms for every non-carbon heavy atom, more preferably at least 3 carbon atoms for every non-carbon heavy atom. The carbon atoms and oxygen atoms are typically present in a ratio of at least 1 carbon atom for every oxygen atom, preferably at least 2 carbon atoms for every oxygen atom, or more preferably at least 3 carbon atoms for every oxygen atom. The oligomer may include one or more capping groups, such as branched or linear $C_{1-6}$, branched or linear, or a carbonyl. The oligomer will typically include hydrogens, and one or more of the hydrogens may be substituted with a fluorine (which is a heavy atom but should not be counted as a heavy atom in the foregoing formula). The oligomer may in some cases specifically exclude unsubstituted alkyl moieties. The oligomer may, for example, be coupled to an available group on an amino acid, such as an amino group, a hydroxyl group or a free carboxylic acid group the polypeptide, e.g., by a linking group, such as a carbamate, carbonate, ether, ester, amide, or secondary amine group, or by a disulfide bond. The molecules in the linking group are counted as part of the oligomer.

Other preferred oligomers include:

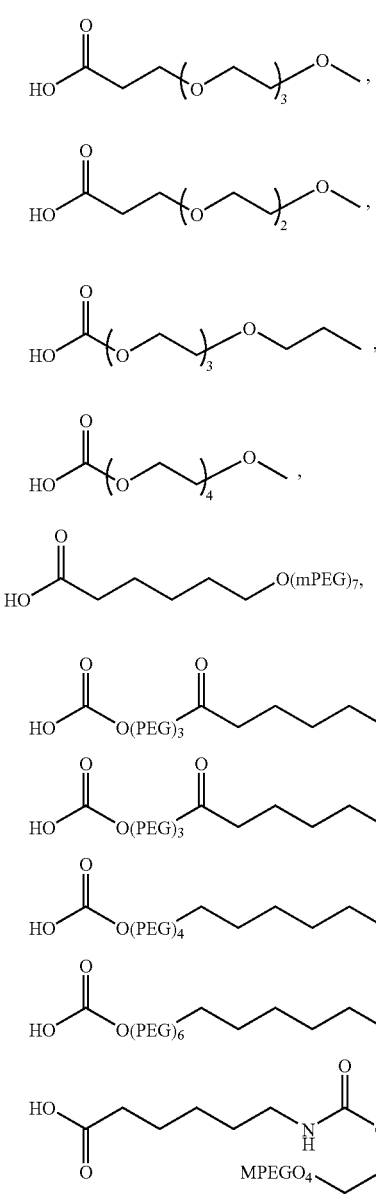

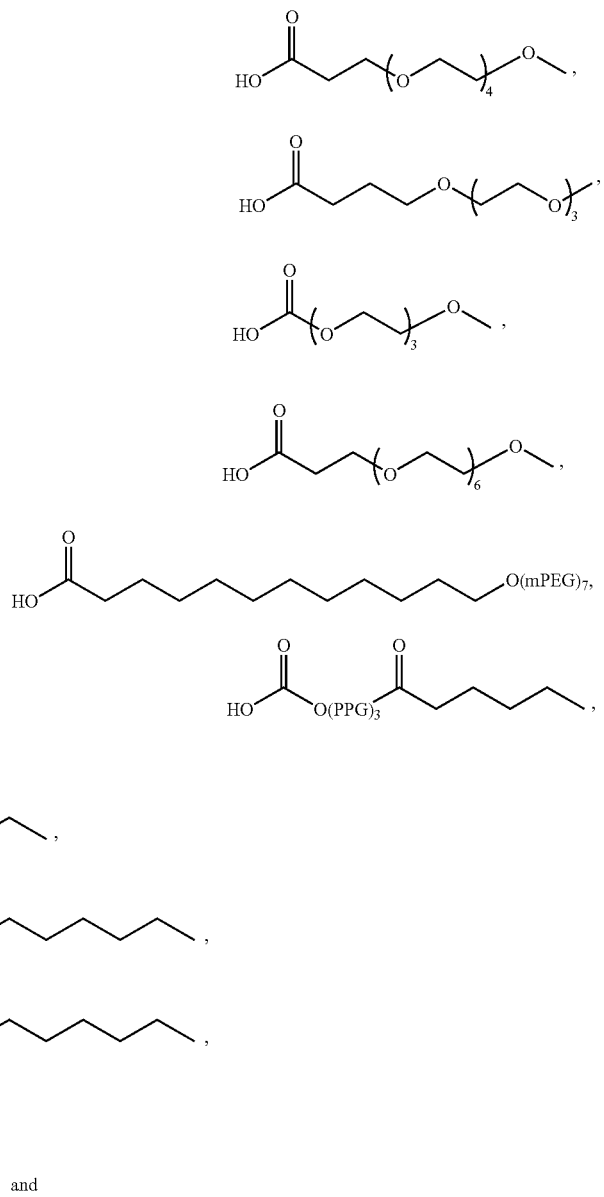

and

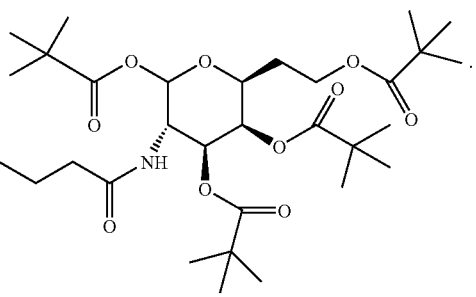

Still other oligomers include the following:
R—CH₂—CH₂—CH₂—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₂—O—CH₂—CH₂—CH₂—CH₃,
R—CH₂—CH₂—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—CH₂—CH₂—O—CH₂—CH₂—O—CH₃,
R—CH₂—CH₂—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₂—O—CH₂—CH₂—CH₂—CH₂—CH₃,
R—CH₂—CH₂—CH₂—CH₂—CH₂—CH₂—CH₂—CH₂—CH₂—O—CH₂—CH₂—CH₂—CH₃,
R—CH₂—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—CH₂—O—CH₂—CH₂—O—CH₂—CH₃, R—CH₂—CH₂—CH₂—CH₂—CH₂—CH₂—CH₂—CH₂—CH₂—O—CH₂—CH₂—O—CH₂—CH₃,
R—CH₂—CH₂—CH₂—CH₂—CH₂—CH₂—CH₂—CH₂—CH₂—O—CH₂—CH₂—O—CH₃,
R—CH₂—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—CH₂—O—CH₃,
R—CH₂—CH₂—CH₂—CH₂—CH₂—CH₂—CH₂—CH₂—CH₃,
R—CH₂—CH₂—CH₂—CH₂—CH₂—CH₂—CH₂—CH₂—CH₃,
R—CH₂—CH₂—CH₂—CH₂—CH₂—CH₂—CH₂—CH₂—O—CH₂—CH₂—CH₂—CH₂—CH₂—CH₃,
R—CH₂—CH₂—CH₂—CH₂—CH₂—CH₂—CH₂—CH₂—O—CH₂—CH₂—CH₂—CH₂—CH₃,
R—CH₂—CH₂—CH₂—CH₂—CH₂—CH₂—CH₂—CH₂—O—CH₂—CH₂—CH₂—CH₃,
R—CH₂—CH₂—CH₂—CH₂—CH₂—CH₂—CH₂—CH₂—O—CH₂—CH₂—CH₂—O—CH₂—CH₃,
R—CH₂—CH₂—CH₂—CH₂—CH₂—CH₂—CH₂—CH₂—O—CH₂—CH₂—O—CH₃,
R—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—CH₂—O—CH₂—CH₂—O—CH₂—CH₃,
R—CH₂—CH₂—CH₂—CH₂—CH₂—CH₂—CH₂—CH₂—O—CH₂—CH₂—O—CH₃,
R—CH₂—CH₂—CH₂—CH₂—CH₂—CH₂—CH₂—CH₂—O—CH₂—CH₃,
R—CH₂—CH₂—CH₂—CH₂—CH₂—CH₂—CH₂—CH₂—O—CH₃,
R—CH₂—CH₂—CH₂—CH₂—CH₂—CH₂—CH₂—CH₃,
R—CH₂—CH₂—CH₂—CH₂—CH₂—CH₂—CH₂—CH₃,
R—CH₂—CH₂—CH₂—CH₂—CH₂—CH₂—CH₂—O—CH₂—CH₂—CH₂—CH₂—CH₂—CH₂—CH₃,
R—CH₂—CH₂—CH₂—CH₂—CH₂—CH₂—CH₂—O—CH₂—CH₂—CH₂—CH₂—CH₂—CH₃,
R—CH₂—CH₂—CH₂—CH₂—CH₂—CH₂—CH₂—O—CH₂—CH₂—CH₂—CH₂—CH₃,
R—CH₂—CH₂—CH₂—CH₂—CH₂—CH₂—CH₂—O—CH₂—CH₂—CH₂—CH₃,
R—CH₂—CH₂—CH₂—CH₂—CH₂—CH₂—CH₂—O—CH₂—CH₂—CH₂—O—CH₂—CH₂—CH₃,
R—CH₂—CH₂—CH₂—CH₂—CH₂—CH₂—CH₂—O—CH₂—CH₂—CH₂—O—CH₂—CH₃,
R—CH₂—CH₂—CH₂—CH₂—CH₂—CH₂—CH₂—O—CH₂—CH₂—CH₂—O—CH₃, R—CH₂—CH₂—CH₂—CH₂—CH₂—CH₂—CH₂—O—CH₂—CH₂—CH₃,
R—CH₂—CH₂—CH₂—CH₂—CH₂—CH₂—CH₂—O—CH₂—CH₂—O—CH₂—CH₂—CH₂—CH₃,
R—CH₂—CH₂—CH₂—CH₂—CH₂—CH₂—CH₂—O—CH₂—CH₂—O—CH₂—CH₂—CH₃,
R—CH₂—CH₂—CH₂—CH₂—CH₂—CH₂—CH₂—O—CH₂—CH₂—O—CH₂—CH₂—O—CH₃,
R—CH₂—CH₂—CH₂—CH₂—CH₂—CH₂—CH₂—O—CH₂—CH₂—O—CH₂—CH₃,
R—CH₂—CH₂—CH₂—CH₂—CH₂—CH₂—CH₂—O—CH₂—CH₂—O—CH₃,
R—CH₂—CH₂—CH₂—CH₂—CH₂—CH₂—CH₂—O—CH₂—CH₃,
R—CH₂—CH₂—CH₂—CH₂—CH₂—CH₂—CH₂—O—CH₂—CH₃,
R—CH₂—CH₂—CH₂—CH₂—CH₂—CH₂—CH₂—O—CH₃,
R—CH₂—CH₂—CH₂—CH₂—CH₂—CH₂—CH₃,
R—CH₂—CH₂—CH₂—CH₂—CH₂—CH₂—CH₃,
R—CH₂—CH₂—CH₂—CH₂—CH₂—CH₂—O—CH₂—CH₂—CH₂—CH₂—CH₂—CH₂—CH₃,
R—CH₂—CH₂—CH₂—CH₂—CH₂—CH₂—O—CH₂—CH₂—CH₂—CH₂—CH₂—CH₃,
R—CH₂—CH₂—CH₂—CH₂—CH₂—CH₂—O—CH₂—CH₂—CH₂—CH₂—CH₃,
R—CH₂—CH₂—CH₂—CH₂—CH₂—CH₂—O—CH₂—CH₂—CH₂—CH₃,
R—CH₂—CH₂—CH₂—CH₂—CH₂—CH₂—O—CH₂—CH₂—CH₃,
R—CH₂—CH₂—CH₂—CH₂—CH₂—CH₂—O—CH₂—CH₂—O—CH₂—CH₂—CH₂—CH₃,
R—CH₂—CH₂—CH₂—CH₂—CH₂—CH₂—O—CH₂—CH₂—O—CH₂—CH₂—CH₃,
R—CH₂—CH₂—CH₂—CH₂—CH₂—CH₂—O—CH₂—CH₂—O—CH₂—CH₂—O—CH₃,
R—CH₂—CH₂—CH₂—CH₂—CH₂—CH₂—O—CH₂—CH₃,
R—CH₂—CH₂—CH₂—CH₂—CH₂—CH₂—O—CH₂—O—CH₂—CH₂—CH₂—CH₂—CH₃,
R—CH₂—CH₂—CH₂—CH₂—CH₂—CH₂—O—CH₂—O—CH₂—CH₂—CH₂—CH₃,
R—CH₂—CH₂—CH₂—CH₂—CH₂—CH₂—O—CH₂—O—CH₂—CH₂—CH₃,
R—CH₂—CH₂—CH₂—CH₂—CH₂—CH₂—O—CH₂—O—CH₂—CH₂—CH₂—O—,
R—CH₂—CH₂—CH₂—CH₂—CH₂—CH₂—O—CH₂—O—CH₂—CH₂—CH₃,
R—CH₂—CH₂—CH₂—CH₂—CH₂—CH₂—O—CH₂—O—CH₂—CH₂—O—CH₂—CH₃,
R—CH₂—CH₂—CH₂—CH₂—CH₂—CH₂—O—CH₂—O—CH₂—CH₂—O—CH₃,
R—CH₂—CH₂—CH₂—CH₂—CH₂—CH₂—O—CH₂—O—CH₂—CH₃,
R—CH₂—CH₂—CH₂—CH₂—CH₂—CH₂—O—CH₂—O—CH₃,
R—CH₂—CH₂—CH₂—CH₂—CH₂—CH₂—O—CH₂—CH₃,
R—CH₂—CH₂—CH₂—CH₂—CH₂—CH₂—O—CH₃,
R—CH₂—CH₂—CH₂—CH₂—CH₂—CH₂—CH₃,
R—CH₂—CH₂—CH₂—CH₂—CH₂—O—CH₂—CH₂—CH₂—CH₂—CH₂—CH₂—CH₃,
R—CH₂—CH₂—CH₂—CH₂—CH₂—O—CH₂—CH₂—CH₂—CH₂—CH₂—CH₃, R—CH₂—CH₂—CH₂—CH₂—CH₂—O—CH₂—CH₂—CH₂—CH₂—CH₃,
R—CH₂—CH₂—CH₂—CH₂—CH₂—O—CH₂—CH₂—CH₂—CH₃,
R—CH₂—CH₂—CH₂—CH₂—CH₂—O—CH₂—CH₂—CH₃,
R—CH₂—CH₂—CH₂—CH₂—CH₂—O—CH₂—CH₃,
R—CH₂—CH₂—CH₂—CH₂—CH₂—O—CH₂—CH₂—CH₂—O—CH₂—CH₂—CH₂—CH₂—CH₃,
R—CH₂—CH₂—CH₂—CH₂—CH₂—O—CH₂—CH₂—O—CH₂—CH₂—CH₂—CH₃,
R—CH₂—CH₂—CH₂—CH₂—CH₂—O—CH₂—CH₂—O—CH₂—CH₂—CH₃,
R—CH₂—CH₂—CH₂—CH₂—CH₂—O—CH₂—CH₂—O—CH₂—CH₂—O—CH₂—CH₃,
R—CH₂—CH₂—CH₂—CH₂—CH₂—O—CH₂—CH₂—O—CH₂—CH₂—O—CH₃,
R—CH₂—CH₂—CH₂—CH₂—CH₂—O—CH₂—CH₂—O—CH₂—CH₃,
R—CH₂—CH₂—CH₂—CH₂—CH₂—O—CH₂—CH₂—O—CH₃,
R—CH₂—CH₂—CH₂—CH₂—CH₂—O—CH₂—CH₃,
R—CH₂—CH₂—CH₂—CH₂—CH₂—O—CH₂—CH₂—CH₂—CH₂—CH₂—O—CH₃,
R—CH₂—CH₂—CH₂—CH₂—CH₂—O—CH₂—CH₃,
R—CH₂—CH₂—CH₂—CH₂—CH₂—O—CH₃,
R—CH₂—CH₂—CH₂—CH₂—O—CH₂—CH₂—,
R—CH₂—CH₂—CH₂—CH₂—O—CH₂—CH₂—CH₂—CH₂—CH₂—CH₂—CH₃,
R—CH₂—CH₂—CH₂—CH₂—O—CH₂—CH₂—CH₂—CH₂—CH₂—CH₃,
R—CH₂—CH₂—CH₂—CH₂—O—CH₂—CH₂—CH₂—CH₂—CH₃,
R—CH₂—CH₂—CH₂—CH₂—O—CH₂—CH₂—CH₂—CH₃,
R—CH₂—CH₂—CH₂—CH₂—O—CH₂—CH₂—CH₃,
R—CH₂—CH₂—CH₂—CH₂—O—CH₂—CH₃,
R—CH₂—CH₂—CH₂—CH₂—O—CH₃,
R—CH₂—CH₂—CH₂—O—CH₂—CH₂—CH₂—O—CH₂—CH₂—CH₂—CH₂—CH₂—CH₃, R—CH₂—CH₂—CH₂—CH₂—O—CH₂—CH₂—CH₂—O—CH₂—CH₂—CH₂—CH₂—CH₃,
R—CH₂—CH₂—CH₂—CH₂—O—CH₂—CH₂—CH₂—O—CH₂—CH₂—CH₂—CH₃,
R—CH₂—CH₂—CH₂—CH₂—O—CH₂—CH₂—CH₂—O—CH₂—CH₂—CH₃,
R—CH₂—CH₂—CH₂—CH₂—O—CH₂—CH₂—CH₂—O—CH₂—CH₂—O—CH₂—CH₂—CH₃,
R—CH₂—CH₂—CH₂—CH₂—O—CH₂—CH₂—CH₂—O—CH₂—CH₂—O—CH₂—CH₃,
R—CH₂—CH₂—CH₂—CH₂—O—CH₂—CH₂—CH₂—O—CH₂—CH₂—O—CH₃,
R—CH₂—CH₂—CH₂—CH₂—O—CH₂—CH₂—CH₂—O—CH₂—CH₃,
R—CH₂—CH₂—CH₂—CH₂—O—CH₂—CH₂—CH₂—O—CH₃,
R—CH₂—CH₂—CH₂—CH₂—O—CH₂—CH₂—CH₃,
R—CH₂—CH₂—CH₂—CH₂—O—CH₂—CH₂—O—CH₂—CH₂—CH₂—CH₂—CH₂—CH₂—CH₃,
R—CH₂—CH₂—CH₂—CH₂—O—CH₂—CH₂—O—CH₂—CH₂—CH₂—CH₂—CH₂—CH₃,
R—CH₂—CH₂—CH₂—CH₂—O—CH₂—CH₂—O—CH₂—CH₂—CH₂—CH₂—CH₃,
R—CH₂—CH₂—CH₂—CH₂—O—CH₂—CH₂—O—CH₂—CH₂—CH₂—CH₃,
R—CH₂—CH₂—CH₂—CH₂—O—CH₂—CH₂—O—CH₂—CH₂—CH₃,
R—CH₂—CH₂—CH₂—CH₂—O—CH₂—CH₂—O—CH₂—CH₂—O—CH₂—CH₂—CH₃,
R—CH₂—CH₂—CH₂—CH₂—O—CH₂—CH₂—O—CH₂—CH₂—CH₂—O—CH₂—CH₃,
R—CH₂—CH₂—CH₂—CH₂—O—CH₂—CH₂—O—CH₂—CH₂—CH₂—O—CH₃,
R—CH₂—CH₂—CH₂—CH₂—O—CH₂—CH₂—O—CH₂—CH₂—CH₃,
R—CH₂—CH₂—CH₂—CH₂—O—CH₂—CH₂—O—CH₂—CH₂—CH₃,
R—CH₂—CH₂—CH₂—CH₂—O—CH₂—CH₂—O—CH₂—CH₂—O—CH₂—CH₂—CH₂—CH₃,
R—CH₂—CH₂—CH₂—CH₂—O—CH₂—CH₂—O—CH₂—CH₂—O—CH₂—CH₂—CH₃,
R—CH₂—CH₂—CH₂—CH₂—O—CH₂—CH₂—O—CH₂—CH₂—O—CH₂—CH₂—O—CH₃,
R—CH₂—CH₂—CH₂—CH₂—O—CH₂—CH₂—O—CH₂—CH₂—O—CH₂—CH₃,
R—CH₂—CH₂—CH₂—CH₂—O—CH₂—CH₂—O—CH₂—CH₂—O—CH₃,
R—CH₂—CH₂—CH₂—CH₂—O—CH₂—CH₂—O—CH₂—CH₃,
R—CH₂—CH₂—CH₂—CH₂—O—CH₂—CH₂—O—CH₂—CH₃,
R—CH₂—CH₂—CH₂—CH₂—O—CH₂—CH₂—O—CH₃,
R—CH₂—CH₂—CH₂—CH₂—O—CH₃,
R—CH₂—CH₂—CH₂—O—CH₂—CH₂—CH₂—CH₂—CH₂—CH₂—CH₂—CH₂—CH₃,
R—CH₂—CH₂—CH₂—O—CH₂—CH₂—CH₂—CH₂—CH₂—CH₂—CH₂—CH₃,
R—CH₂—CH₂—CH₂—O—CH₂—CH₂—CH₂—CH₂—CH₂—CH₂—CH₃,
R—CH₂—CH₂—CH₂—O—CH₂—CH₂—CH₂—CH₂—CH₂—CH₂—CH₃,
R—CH₂—CH₂—CH₂—O—CH₂—CH₂—CH₂—CH₂—CH₂—CH₃,
R—CH₂—CH₂—CH₂—O—CH₂—CH₂—CH₂—CH₂—CH₃,
R—CH₂—CH₂—CH₂—O—CH₂—CH₂—CH₂—CH₂—CH₃, R—CH₂—CH₂—CH₂—O—CH₂—CH₂—CH₂—CH₂—O—CH₂—CH₂—CH₂—,
R—CH₂—CH₂—CH₂—O—CH₂—CH₂—CH₂—O—CH₂—CH₂—CH₂—CH₂—,
R—CH₂—CH₂—CH₂—O—CH₂—CH₂—CH₂—O—CH₂—CH₂—O—CH₂—,
R—CH₂—CH₂—CH₂—O—CH₂—CH₂—CH₂—O—CH₂—CH₃,
R—CH₂—CH₂—CH₂—O—CH₂—CH₂—CH₂—O—CH₃,
R—CH₂—CH₂—CH₂—O—CH₂—CH₂—CH₂—CH₃,
R—CH₂—CH₂—CH₂—O—CH₂—CH₂—CH₂—O—CH₂—CH₂—CH₂—CH₂—CH₂—CH₂—CH₃,
R—CH₂—CH₂—CH₂—O—CH₂—CH₂—CH₂—O—CH₂—CH₂—CH₂—CH₂—CH₂—CH₃,
R—CH₂—CH₂—CH₂—O—CH₂—CH₂—CH₂—O—CH₂—CH₂—CH₂—CH₂—CH₃,
R—CH₂—CH₂—CH₂—O—CH₂—CH₂—CH₂—O—CH₂—CH₂—CH₂—CH₃,
R—CH₂—CH₂—CH₂—O—CH₂—CH₂—CH₂—O—CH₂—CH₂—CH₃,
R—CH₂—CH₂—CH₂—O—CH₂—CH₂—CH₂—O—CH₂—CH₂—O—CH₂—CH₂—CH₂—CH₃,
R—CH₂—CH₂—CH₂—O—CH₂—CH₂—CH₂—O—CH₂—CH₂—O—CH₂—CH₂—CH₃,
R—CH₂—CH₂—CH₂—O—CH₂—CH₂—CH₂—O—CH₂—CH₂—O—CH₂—CH₃,
R—CH₂—CH₂—CH₂—O—CH₂—CH₂—CH₂—O—CH₂—CH₂—O—CH₃,
R—CH₂—CH₂—CH₂—O—CH₂—CH₂—CH₂—O—CH₂—CH₃,
R—CH₂—CH₂—CH₂—O—CH₂—CH₂—CH₂—O—CH₃,
R—CH₂—CH₂—CH₂—O—CH₂—CH₂—CH₃,
R—CH₂—CH₂—CH₂—O—CH₂—CH₂—O—CH₂—CH₂—CH₂—CH₂—CH₂—CH₂—CH₃,
R—CH₂—CH₂—CH₂—O—CH₂—CH₂—O—CH₂—CH₂—CH₂—CH₂—CH₂—CH₃,
R—CH₂—CH₂—CH₂—O—CH₂—CH₂—O—CH₂—CH₂—CH₂—CH₂—CH₃,
R—CH₂—CH₂—CH₂—O—CH₂—CH₂—O—CH₂—CH₂—CH₂—CH₃,
R—CH₂—CH₂—CH₂—O—CH₂—CH₂—O—CH₂—CH₂—CH₃,
R—CH₂—CH₂—CH₂—O—CH₂—CH₂—O—CH₂—CH₂—O—CH₂—CH₂—CH₂—CH₃,
R—CH₂—CH₂—CH₂—O—CH₂—CH₂—O—CH₂—CH₂—O—CH₂—CH₂—CH₃,
R—CH₂—CH₂—CH₂—O—CH₂—CH₂—O—CH₂—CH₂—O—CH₂—CH₃,
R—CH₂—CH₂—CH₂—O—CH₂—CH₂—O—CH₂—CH₂—O—CH₃,
R—CH₂—CH₂—CH₂—O—CH₂—CH₂—O—CH₂—CH₃,
R—CH₂—CH₂—CH₂—O—CH₂—CH₂—O—CH₂—CH₂—O—CH₂—CH₂—CH₂—CH₂—CH₃,
R—CH₂—CH₂—CH₂—O—CH₂—CH₂—O—CH₂—CH₂—O—CH₂—CH₂—CH₂—CH₃,
R—CH₂—CH₂—CH₂—O—CH₂—CH₂—O—CH₂—CH₂—O—CH₂—CH₂—CH₃, R—CH₂—CH₂—CH₂—O—CH₂—CH₂—O—CH₂—CH₂—O—CH₂—CH₂—O—CH₂—CH₃,
R—CH₂—CH₂—CH₂—O—CH₂—CH₂—O—CH₂—CH₂—O—CH₂—CH₂—O—CH₃,
R—CH₂—CH₂—CH₂—O—CH₂—CH₂—O—CH₂—CH₂—O—CH₂—CH₃,
R—CH₂—CH₂—CH₂—O—CH₂—CH₂—O—CH₂—CH₂—O—CH₃,
R—CH₂—CH₂—CH₂—O—CH₂—CH₂—O—CH₂—CH₃,
R—CH₂—CH₂—CH₂—O—CH₂—CH₂—O—CH₃,
R—CH₂—CH₂—CH₂—O—CH₂—CH₃,
R—CH₂—CH₂—CH₂—O—CH₃,
R—CH₂—CH₂—O—CH₂—CH₂—CH₂—CH₂—CH₂—CH₂—CH₂—CH₂—CH₂—CH₂—CH₃,
R—CH₂—CH₂—O—CH₂—CH₂—CH₂—CH₂—CH₂—CH₂—CH₂—CH₂—CH₂—CH₃,
R—CH₂—CH₂—O—CH₂—CH₂—CH₂—CH₂—CH₂—CH₂—CH₂—CH₂—CH₃,
R—CH₂—CH₂—O—CH₂—CH₂—CH₂—CH₂—CH₂—CH₂—CH₂—CH₃,
R—CH₂—CH₂—O—CH₂—CH₂—CH₂—CH₂—CH₂—CH₂—CH₃,
R—CH₂—CH₂—O—CH₂—CH₂—CH₂—CH₂—CH₂—CH₃,
R—CH₂—CH₂—O—CH₂—CH₂—CH₂—CH₂—CH₃,
R—CH₂—CH₂—O—CH₂—CH₂—CH₂—CH₃,
R—CH₂—CH₂—O—CH₂—CH₂—CH₂—CH₂—O—CH₂—CH₂—CH₂—CH₂—CH₃,
R—CH₂—CH₂—O—CH₂—CH₂—CH₂—CH₂—O—CH₂—CH₂—CH₂—CH₃,
R—CH₂—CH₂—O—CH₂—CH₂—CH₂—CH₂—O—CH₂—CH₂—CH₂—O—CH₃,
R—CH₂—CH₂—O—CH₂—CH₂—CH₂—CH₂—O—CH₂—CH₂—CH₃,
R—CH₂—CH₂—O—CH₂—CH₂—CH₂—CH₂—O—CH₂—CH₂—O—CH₂—CH₃,
R—CH₂—CH₂—O—CH₂—CH₂—CH₂—CH₂—O—CH₂—CH₂—O—CH₃,
R—CH₂—CH₂—O—CH₂—CH₂—CH₂—CH₂—O—CH₂—CH₃,
R—CH₂—CH₂—O—CH₂—CH₂—CH₂—CH₂—O—CH₃,
R—CH₂—CH₂—O—CH₂—CH₂—CH₂—CH₃,
R—CH₂—CH₂—O—CH₂—CH₂—CH₂—O—CH₂—CH₂—CH₂—CH₂—CH₂—CH₂—CH₃,
R—CH₂—CH₂—O—CH₂—CH₂—CH₂—O—CH₂—CH₂—CH₂—CH₂—CH₂—CH₃,
R—CH₂—CH₂—O—CH₂—CH₂—CH₂—O—CH₂—CH₂—CH₂—CH₂—CH₃,
R—CH₂—CH₂—O—CH₂—CH₂—CH₂—O—CH₂—CH₂—CH₂—CH₃,
R—CH₂—CH₂—O—CH₂—CH₂—CH₂—O—CH₂—CH₂—CH₃,
R—CH₂—CH₂—O—CH₂—CH₂—CH₂—O—CH₂—CH₃,
R—CH₂—CH₂—O—CH₂—CH₂—CH₂—O—CH₂—CH₂—O—CH₂—CH₂—CH₂—CH₂—CH₃,
R—CH₂—CH₂—O—CH₂—CH₂—CH₂—O—CH₂—CH₂—O—CH₂—CH₂—CH₃,
R—CH₂—CH₂—O—CH₂—CH₂—CH₂—O—CH₂—CH₂—O—CH₂—CH₃,
R—CH₂—CH₂—O—CH₂—CH₂—CH₂—O—CH₂—CH₂—O—CH₂—CH₂—O—CH₂—CH₃,
R—CH₂—CH₂—O—CH₂—CH₂—CH₂—O—CH₂—CH₂—O—CH₂—CH₂—O—CH₃,
R—CH₂—CH₂—O—CH₂—CH₂—CH₂—O—CH₂—CH₂—O—CH₂—CH₃, R—CH₂—CH₂—O—CH₂—CH₂—CH₂—O—CH₂—O—CH₃,
R—CH₂—CH₂—O—CH₂—CH₂—CH₂—O—CH₂—CH₃,
R—CH₂—CH₂—O—CH₂—CH₂—CH₂—O—CH₃,
R—CH₂—CH₂—O—CH₂—CH₂—O—CH₂—CH₂—CH₂—CH₂—CH₂—CH₂—CH₃,
R—CH₂—CH₂—O—CH₂—CH₂—O—CH₂—CH₂—CH₂—CH₂—CH₂—CH₃,
R—CH₂—CH₂—O—CH₂—CH₂—O—CH₂—CH₂—CH₂—CH₂—CH₃,
R—CH₂—CH₂—O—CH₂—CH₂—O—CH₂—CH₂—CH₂—CH₃,
R—CH₂—CH₂—O—CH₂—CH₂—O—CH₂—CH₂—CH₃,
R—CH₂—CH₂—O—CH₂—CH₂—O—CH₂—CH₃,
R—CH₂—CH₂—O—CH₂—CH₂—O—CH₂—CH₃,
R—CH₂—CH₂—O—CH₂—CH₂—O—CH₂—CH₂—O—CH₂—CH₂—CH₂—CH₂—CH₃,
R—CH₂—CH₂—O—CH₂—CH₂—O—CH₂—CH₂—O—CH₂—CH₂—CH₂—CH₃,
R—CH₂—CH₂—O—CH₂—CH₂—O—CH₂—CH₂—O—CH₂—CH₂—CH₃,
R—CH₂—CH₂—O—CH₂—CH₂—O—CH₂—CH₂—O—CH₂—CH₃,
R—CH₂—CH₂—O—CH₂—CH₂—O—CH₂—CH₂—O—CH₂—CH₃,
R—CH₂—CH₂—O—CH₂—CH₂—O—CH₂—CH₂—O—CH₂—CH₃,
R—CH₂—CH₂—O—CH₂—CH₂—O—CH₂—CH₂—O—CH₂—CH₂—CH₂—CH₂—CH₃,
R—CH₂—CH₂—O—CH₂—CH₂—O—CH₂—CH₂—O—CH₂—CH₂—CH₂—CH₃,
R—CH₂—CH₂—O—CH₂—CH₂—O—CH₂—CH₂—O—CH₂—CH₂—CH₃,
R—CH₂—CH₂—O—CH₂—CH₂—O—CH₂—CH₂—O—CH₂—CH₃,
R—CH₂—CH₂—O—CH₂—CH₂—O—CH₂—CH₂—O—CH₃,
R—CH₂—CH₂—O—CH₂—CH₂—O—CH₂—CH₃,
R—CH₂—CH₂—O—CH₂—CH₂—O—CH₃,
R—CH₂—CH₂—O—CH₂—CH₃,
R—CH₂—CH₂—O—CH₃,
R—CH₂—O—CH₂—CH₂—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₃,
R—CH₂—O—CH₂—CH₂—CH₂—CH₂—CH₂—CH₂—CH₃,
R—CH₂—O—CH₂—CH₂—CH₂—CH₂—CH₂—O—CH₃, R—CH₂—O—CH₂—CH₂—CH₂—CH₂—CH₂—CH₂—CH₂—CH₂—CH₃,
R—CH₂—O—CH₂—CH₂—CH₂—CH₂—CH₂—CH₂—CH₂—CH₂—O—CH₂—CH₃,
R—CH₂—O—CH₂—CH₂—CH₂—CH₂—CH₂—CH₂—CH₂—CH₂—O—CH₃,
R—CH₂—O—CH₂—CH₂—CH₂—CH₂—CH₂—CH₂—CH₂—CH₃,
R—CH₂—O—CH₂—CH₂—CH₂—CH₂—CH₂—CH₂—CH₂—O—CH₂—CH₂—CH₃,
R—CH₂—O—CH₂—CH₂—CH₂—CH₂—CH₂—CH₂—CH₂—O—CH₂—CH₃,
R—CH₂—O—CH₂—CH₂—CH₂—CH₂—CH₂—CH₂—CH₂—O—CH₃,
R—CH₂—O—CH₂—CH₂—CH₂—CH₂—CH₂—CH₂—CH₃,
R—CH₂—O—CH₂—CH₂—CH₂—CH₂—CH₂—CH₂—O—CH₂—CH₂—CH₂—CH₃,
R—CH₂—O—CH₂—CH₂—CH₂—CH₂—CH₂—CH₂—O—CH₂—CH₂—CH₃,
R—CH₂—O—CH₂—CH₂—CH₂—CH₂—CH₂—CH₂—O—CH₂—CH₂—O—CH₃,
R—CH₂—O—CH₂—CH₂—CH₂—CH₂—CH₂—CH₂—O—CH₂—CH₃,
R—CH₂—O—CH₂—CH₂—CH₂—CH₂—CH₂—CH₂—O—CH₃,
R—CH₂—O—CH₂—CH₂—CH₂—CH₂—CH₂—CH₃,
R—CH₂—O—CH₂—CH₂—CH₂—CH₂—CH₂—O—CH₂—CH₂—CH₂—CH₂—CH₃,
R—CH₂—O—CH₂—CH₂—CH₂—CH₂—CH₂—O—CH₂—CH₂—CH₂—CH₂—CH₃,
R—CH₂—O—CH₂—CH₂—CH₂—CH₂—CH₂—O—CH₂—CH₂—CH₂—CH₃,
R—CH₂—O—CH₂—CH₂—CH₂—CH₂—CH₂—O—CH₂—CH₂—CH₂—O—CH₃,
R—CH₂—O—CH₂—CH₂—CH₂—CH₂—CH₂—O—CH₂—CH₂—CH₃,
R—CH₂—O—CH₂—CH₂—CH₂—CH₂—CH₂—O—CH₂—CH₂—O—CH₂—CH₃,
R—CH₂—O—CH₂—CH₂—CH₂—CH₂—CH₂—O—CH₂—CH₂—O—CH₃,
R—CH₂—O—CH₂—CH₂—CH₂—CH₂—CH₂—O—CH₂—CH₃,
R—CH₂—O—CH₂—CH₂—CH₂—CH₂—CH₂—CH₃,
R—CH₂—O—CH₂—CH₂—CH₂—CH₂—O—CH₂—CH₂—CH₂—CH₂—CH₃,
R—CH₂—O—CH₂—CH₂—CH₂—CH₂—O—CH₂—CH₂—CH₂—CH₃,
R—CH₂—O—CH₂—CH₂—CH₂—CH₂—O—CH₂—CH₂—CH₂—O—CH₃,
R—CH₂—O—CH₂—CH₂—CH₂—CH₂—O—CH₂—CH₂—CH₃,
R—CH₂—O—CH₂—CH₂—CH₂—CH₂—O—CH₂—CH₂—O—CH₂—CH₃,
R—CH₂—O—CH₂—CH₂—CH₂—CH₂—O—CH₂—CH₂—O—CH₃,
R—CH₂—O—CH₂—CH₂—CH₂—CH₂—O—CH₂—CH₃,
R—CH₂—O—CH₂—CH₂—CH₂—CH₂—O—CH₂—O—CH₂—CH₂—CH₃,
R—CH₂—O—CH₂—CH₂—CH₂—CH₂—O—CH₂—O—CH₂—CH₃,
R—CH₂—O—CH₂—CH₂—CH₂—CH₂—O—CH₂—O—CH₃,
R—CH₂—O—CH₂—CH₂—CH₂—CH₂—O—CH₂—CH₃,
R—CH₂—O—CH₂—CH₂—CH₂—CH₂—O—CH₃,
R—CH₂—O—CH₂—CH₂—CH₂—CH₂—CH₃, R—CH₂—O—CH₂—CH₂—CH₂—O—CH₂—CH₂—CH₂—CH₂—CH₂—CH₂—CH₃,
R—CH₂—O—CH₂—CH₂—CH₂—O—CH₂—CH₂—CH₂—CH₂—CH₂—CH₃,
R—CH₂—O—CH₂—CH₂—CH₂—O—CH₂—CH₂—CH₂—CH₂—CH₃,
R—CH₂—O—CH₂—CH₂—CH₂—O—CH₂—CH₂—CH₂—CH₃,
R—CH₂—O—CH₂—CH₂—CH₂—O—CH₂—CH₂—CH₂—CH₃,
R—CH₂—O—CH₂—CH₂—CH₂—O—CH₂—CH₂—CH₃,
R—CH₂—O—CH₂—CH₂—CH₂—O—CH₂—CH₂—CH₃,
R—CH₂—O—CH₂—CH₂—CH₂—O—CH₂—CH₂—CH₃,
R—CH₂—O—CH₂—CH₂—CH₂—O—CH₂—CH₂—CH₃,
R—CH₂—O—CH₂—CH₂—CH₂—O—CH₂—CH₂—O—CH₂—CH₂—CH₂—CH₂—CH₂—CH₃,
R—CH₂—O—CH₂—CH₂—CH₂—O—CH₂—CH₂—O—CH₂—CH₂—CH₂—CH₂—CH₃,
R—CH₂—O—CH₂—CH₂—CH₂—O—CH₂—CH₂—O—CH₂—CH₂—CH₂—CH₃,
R—CH₂—O—CH₂—CH₂—CH₂—O—CH₂—CH₂—O—CH₂—CH₂—CH₃,
R—CH₂—O—CH₂—CH₂—CH₂—O—CH₂—CH₂—O—CH₂—CH₂—O—CH₂—CH₂—CH₃,
R—CH₂—O—CH₂—CH₂—CH₂—O—CH₂—CH₂—O—CH₂—CH₂—O—CH₂—CH₃,
R—CH₂—O—CH₂—CH₂—CH₂—O—CH₂—CH₂—O—CH₂—CH₂—O—CH₃,
R—CH₂—O—CH₂—CH₂—CH₂—O—CH₂—CH₂—O—CH₂—CH₃,
R—CH₂—O—CH₂—CH₂—CH₂—O—CH₂—CH₂—O—CH₃,
R—CH₂—O—CH₂—CH₂—CH₃,
R—CH₂—O—CH₂—CH₂—O—CH₂—CH₂—,
R—CH₂—O—CH₂—CH₂—O—CH₂—CH₂—CH₂—CH₂—CH₂—CH₂—CH₃,
R—CH₂—O—CH₂—CH₂—O—CH₂—CH₂—CH₂—CH₂—CH₂—CH₂—CH₃,
R—CH₂—O—CH₂—CH₂—O—CH₂—CH₂—CH₂—CH₂—CH₂—CH₃,
R—CH₂—O—CH₂—CH₂—O—CH₂—CH₂—CH₂—CH₂—CH₂—CH₃,
R—CH₂—O—CH₂—CH₂—O—CH₂—CH₂—CH₂—CH₂—CH₃,
R—CH₂—O—CH₂—CH₂—O—CH₂—CH₂—CH₂—CH₃,
R—CH₂—O—CH₂—CH₂—O—CH₂—CH₂—CH₂—CH₃,
R—CH₂—O—CH₂—CH₂—O—CH₂—CH₂—CH₃,
R—CH₂—O—CH₂—CH₂—O—CH₂—CH₂—CH₂—CH₂—CH₂—CH₃,
R—CH₂—O—CH₂—CH₂—O—CH₂—CH₂—CH₂—CH₂—CH₂—CH₃,
R—CH₂—O—CH₂—CH₂—O—CH₂—CH₂—CH₂—O—CH₂—CH₂—CH₂—CH₂—CH₃,
R—CH₂—O—CH₂—CH₂—O—CH₂—CH₂—CH₂—O—CH₂—CH₂—CH₂—CH₃,
R—CH₂—O—CH₂—CH₂—O—CH₂—CH₂—CH₂—O—CH₂—CH₂—CH₃,
R—CH₂—O—CH₂—CH₂—O—CH₂—CH₂—CH₂—O—CH₂—CH₃,
R—CH₂—O—CH₂—CH₂—O—CH₂—CH₂—CH₂—O—CH₂—CH₂—O—CH₃,
R—CH₂—O—CH₂—CH₂—O—CH₂—CH₂—CH₂—O—CH₂—CH₃, R—CH$_2$—O—CH$_2$—CH$_2$—O—CH$_2$—CH$_2$—CH$_2$—O—CH$_3$,
R—CH$_2$—O—CH$_2$—CH$_2$—O—CH$_2$—CH$_2$—CH$_3$,
R—CH$_2$—O—CH$_2$—CH$_2$—O—CH$_2$—CH$_2$—O—CH$_2$—CH$_2$—CH$_2$—CH$_2$—CH$_2$—CH$_3$,
R—CH$_2$—O—CH$_2$—CH$_2$—O—CH$_2$—CH$_2$—O—CH$_2$—CH$_2$—CH$_2$—CH$_2$—CH$_3$,
R—CH$_2$—O—CH$_2$—CH$_2$—O—CH$_2$—CH$_2$—O—CH$_2$—CH$_2$—CH$_2$—CH$_3$,
R—CH$_2$—O—CH$_2$—CH$_2$—O—CH$_2$—CH$_2$—O—CH$_2$—CH$_2$—CH$_2$—CH$_3$,
R—CH$_2$—O—CH$_2$—CH$_2$—O—CH$_2$—CH$_2$—O—CH$_2$—CH$_2$—CH$_3$,
R—CH$_2$—O—CH$_2$—CH$_2$—O—CH$_2$—CH$_2$—O—CH$_2$—O—CH$_2$—CH$_2$—CH$_2$—CH$_3$,
R—CH$_2$—O—CH$_2$—CH$_2$—O—CH$_2$—CH$_2$—O—CH$_2$—O—CH$_2$—CH$_2$—CH$_3$,
R—CH$_2$—O—CH$_2$—CH$_2$—O—CH$_2$—CH$_2$—O—CH$_2$—O—CH$_2$—CH$_2$—O—CH$_3$,
R—CH$_2$—O—CH$_2$—CH$_2$—O—CH$_2$—CH$_2$—O—CH$_2$—O—CH$_2$—CH$_3$,
R—CH$_2$—O—CH$_2$—CH$_2$—O—CH$_2$—CH$_2$—O—CH$_2$—O—CH$_3$,
R—CH$_2$—O—CH$_2$—CH$_2$—O—CH$_2$—CH$_2$—O—CH$_2$—CH$_3$,
R—CH$_2$—O—CH$_2$—CH$_2$—O—CH$_2$—CH$_2$—O—CH$_3$,
R—CH$_2$—O—CH$_2$—CH$_2$—O—CH$_3$,
R—CH$_2$—O—CH$_2$—CH$_3$,
R—CH$_2$—O—CH$_3$,
where R is —H, —OH, —CH$_2$OH, —CH(OH)$_2$, —C(O)OH, —CH$_2$C(O)OH, or an activating moiety, such as a carbodiimide, a mixed anhydride, or an N-hydroxysuccinimide, or a capping group.

The invention also includes such moieties attached to a GLP-1 compound or an exenatide compound. Specific conjugation strategies are discussed in more detail below. In some embodiments, the oligomer is selected to render the GLP-1 compound or exenatide compound less lipophilic and/or more hydrophilic than the corresponding unconjugated compound. In some embodiments, the oligomer is selected to render the GLP-1 compound or exenatide compound less hydrophilic and/or more lipophilic than the corresponding unconjugated compound. The invention includes such oligomers further including one or more carbonyl groups, preferably 1, 2, 3, 4, or 5 carbonyl groups; the carbonyl groups may be inserted into the oligomer, or an —O— or —CH$_2$— may be replaced with a carbonyl. Further, any of the —CH$_2$— or —CH$_3$ moieties may be substituted, e.g., with a lower alkyl or an —OH or a PAG chain having 1, 2, 3, 4, or 5 PAG subunits, which may be the same or different. Preferably, R is selected so that each —O— is separated from the nearest —O— by at least 2 carbons. The invention also includes branched oligomers in which two or more of the moieties are attached to a branching moiety, such as a lysine.

Exemplary syntheses are described in the examples set forth below. The reaction conditions (e.g., selected molar ratios, solvent mixtures and/or pH) may be controlled according to known principles. For example, conjugation at the amino functionality of lysine may be suppressed by maintaining the pH of the reaction solution below the pK$_a$ of lysine.

The mixture of conjugates may be separated and isolated utilizing, for example, HPLC to provide conjugates, for example mono-, di-, or tri-conjugates. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., Lys$^{12}$, Lys$^{27}$, or the N-terminus of exenatide monoconjugate) may be determined and/or verified utilizing various techniques as will be understood by those skilled in the art including, but not limited to, sequence analysis, peptide mapping, selective enzymatic cleavage, and/or endopeptidase cleavage.

The conjugates may be formulated for administration in a pharmaceutical carrier in accordance with known techniques. See, e.g., Alfonso R. Gennaro, Remington: The Science and Practice of Pharmacy, Lippincott Williams & Wilkins Publishers (June 2003), and Howard C. Ansel, Pharmaceutical Dosage Forms and Drug Delivery Systems, Lippincott Williams & Wilkins Publishers, 7th ed. (October 1999), the entire disclosures of which are incorporated herein by reference for their teachings concerning the selection, making and using of pharmaceutical dosage forms.

The complexes, typically in the form of an amorphous or crystalline solid, can be combined with a pharmaceutically acceptable carrier. The carrier must be acceptable in the sense of being compatible with any other ingredients in the pharmaceutical composition and should not be unduly deleterious to the subject, relative to the benefit provided by the active ingredient(s). The carrier may be a solid or a liquid, or both. It is preferably formulated as a unit-dose formulation, for example, a tablet. The unit dosage form may, for example, contain from about 0.01 or 0.5% to about 95% or 99% by weight of the metabolic compound conjugate.

The pharmaceutical compositions may be prepared by any of the well known techniques of pharmacy including, but not limited to, admixing the components, optionally including one or more accessory ingredients.

Preferred oral compositions are compositions prepared for ingestion by the subject. Ideally, the oral compositions are prepared to survive or substantially survive passage through the stomach and to completely or substantially completely dissolve in the intestine for delivery of the active ingredient. The formulation may in some cases include an enteric coating, and in some cases, the formulation will specifically exclude an enteric coating. The composition is preferably provided as a tablet, powder, hard gelatin capsule, or soft gelatin capsule, though other forms described herein are suitable as well. For example, the composition oral administration may be presented in discrete units, such as capsules, cachets, lozenges, or tables, each containing a predetermined amount of the mixture of metabolic compound conjugates; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the mixture of insulin compound conjugates and a suitable carrier (which may contain one or more accessory ingredients as noted above).

In general, the pharmaceutical compositions of the invention are prepared by uniformly and intimately admixing the conjugates with a liquid or solid carrier, or both, and then, if necessary, shaping the resulting mixture. For example, a tablet may be prepared by compressing or molding a powder or granules containing the mixture of metabolic compound conjugates, optionally with one or more accessory ingredients. Compressed tablets may be prepared by compressing, in a suitable machine, the mixture in a free-flowing form, such as a powder or granules optionally mixed with a binder, lubricant, inert diluent, and/or surface active/dispersing agent(s). Molded tablets may be made by molding, in a suitable machine, the powdered composition moistened with an inert liquid binder.

The effective amount of the metabolic compound conjugate composition for administration according to the methods of the invention will vary somewhat from mixture to mixture, and subject to subject, and will depend upon factors such as the age and condition of the subject, the route of delivery and the condition being treated. Such dosages can be determined in accordance with routine pharmacological procedures known to those skilled in the art noting that the metabolic compound conjugates have a glucose-dependent action where insulin release is attenuated at lower blood glucose concentrations and thus dosage can be determined without risking the induction of a hypoglycaemic event.

Blood glucose level is kept below an upper limit which is about 110 mg/dL, about 120 mg/dL or about 130 mg/dL. More specifically, blood glucose level is clamped within a range where the lower limit can be selected to be about 60, about 70 or about 80 mg/dL and the upper limit can be selected to be about 110, about 120 or about 130 mg/dL, more specifically to the normal range (i.e., from about 80 to about 110 mg/dL). The skilled art worker, for example, the physician, will be able to decide exactly which upper and lower limits to use. Alternatively, the range is from about 60 to about 130, preferably, from about 70 to about 120, more preferred, from about 80 to about 110 mg/dL.

As a general proposition, an oral dosage from about 0.025 to about 10 mg/kg of active ingredient (i.e., the conjugate) will have therapeutic efficacy, with all weights being calculated based upon the weight of the mixture of metabolic compound conjugates. A more preferred range is about 0.06 to about 1 mg/kg, and an even more preferred range is about 0.125 to about 0.5 mg/kg. The dosage of the metabolic compound, such as GLP-1 or exenatide included in the conjugates is generally in an amount from about 0.1 µg/kg/day to about 20 µg/kg/day.

The ensuing examples are illustrative of the practice of the invention using exenatide or GLP-1. However, it will be understood that a similar approach can be used with regard to analogs, fragments, truncations, and isoforms of exenatide or GLP-1, as described above and as will be understood by those skilled in the art.

EXAMPLES

The feasibility of an oral exenatide or GLP-1 compound is demonstrated by synthesizing an amphiphilic polymer conjugate of exenatide or GLP-1, testing the conjugate for cAMP-releasing ability, evaluating its resistance to proteolytic degradation, and measuring activity after oral administration. Once the conjugate is synthesized, verified that it has agonist activity on the GLP-1 receptor, observed an increased resistance to proteases, and confirmed that it is orally active, the pharmacokinetic and pharmacodynamic properties of the exenatide or GLP-1 conjugate are examined in vivo. Refinements can be made with the conjugate synthesis and design as results are obtained from the cellular, biochemical, and in vivo assays.

Synthesis of an Amphiphilic Polymer Conjugate of Exenatide or GLP-1

By using amphiphilic oligomers of different size and chemical composition, the absorption and partitioning properties of the exenatide or GLP-1 conjugates can be altered. Conjugate screening is used to determine which of the conjugates retain the activity of the native peptide and show enhanced resistance to enzymes. The conjugates that have a desirable combination of traits (e.g., agonist activity at the receptor, resistance to proteolysis, and oral bioactivity) may become lead candidates for more extensive in vivo testing.

Synthesis and Design of Exenatide and GLP-1 Conjugates.

The synthetic exenatide or GLP-1 can be synthesized by a contract peptide synthesis company using established methods of chemical synthesis. The conjugation strategy includes three basic classes of oligomers, which are described herein. A preferred conjugation site is the N-terminus or the side chain of a lysine residue.

A first class of conjugates is non-hydrolyzable. For conjugates of this class, the drug substance that is dosed (i.e., the conjugate) is the substance that acts at the receptor. In other words, the oligomer and its attachment to the peptide remain intact from the time of dosing to the time of clearance. These oligomers may generally be comprised of an alkyl portion and a PEG portion. To maximize the effectiveness of the oligomer to make the conjugate orally available and resistant to proteolysis, the lengths of the alkyl and PEG portions can be altered and the order can be switched. The extent of conjugation (e.g. mono- or di-conjugate) can also be manipulated. Some oligomers that can provide conjugates falling within this first class as well as methods for providing such conjugates are described in U.S. Pat. No. 5,359,030 to Ekwuribe; U.S. Pat. No. 5,438,040 to Ekwuribe; U.S. Pat. No. 5,681,811 to Ekwuribe; U.S. Pat. No. 6,191,105 to Ekwuribe; U.S. application Ser. No. 09/474,915, filed Dec. 31, 1999; U.S. application Ser. No. 09/459,443, filed Dec. 13, 1999; and U.S. application Ser. No. 09/873,797, filed Jun. 4, 2001, the disclosures of which are incorporated by reference herein in their entireties.

A second class of conjugates is micropegylated. For conjugates of this class, the alkyl portion of the oligomer is cleaved once the conjugate is in the bloodstream. These conjugates may be particularly useful when conjugation occurs within a region that is necessary for binding. In such cases, the first class of oligomers may be beneficial to stability and delivery, but may be detrimental to activity. The second class of conjugates reduces or eliminates that problem. The amphiphilic oligomer remains intact through the digestive tract and enhances absorption in the upper duodenum. Once in circulation, the alkyl portion is cleaved. Thus, a smaller oligomer is attached to the circulating peptide when it reaches the receptor. In some embodiments, the decreased steric hindrance leads to increased activity at the receptor. Some oligomers that can provide conjugates falling within this second class as well as methods for providing such conjugates are described in U.S. Pat. No. 6,309,633 to Ekwuribe et al. and U.S. application Ser. No. 10/018,879, filed Dec. 19, 2001, the disclosures of which are incorporated by reference herein in their entireties.

A third class of conjugates is fully hydrolyzable. For conjugates of this class, the entire oligomer is cleaved once the conjugate is absorbed. Like the second class, these conjugates may be particularly useful when conjugation occurs within a region that is necessary for binding. However, in the event that the micropegylated conjugates still do not retain sufficient activity, the third class of conjugates may completely obviate the possibility of the oligomer interfering with receptor binding. In this case, the conjugate remains intact through the digestive tract. Once the conjugate is absorbed, the oligomer is cleaved, which releases the native peptide in circulation.

Conjugation of Exenatide and GLP-1.

Activated oligomers are attached to the peptide either in aqueous or DMSO solution. Both exenatide and GLP-1 have 3 sites for conjugation: two lysine residues and the N-termini. By varying the stoichiometry of the reaction, the extent of conjugation (mono-, di-, etc.) can be controlled. Product distribution can be altered by varying the reaction conditions. As preferred sites for conjugation are discovered through the activity assays, preferential synthesis of the desired conjugates can be obtained by varying the stoichiometry and the reaction conditions. In the case of GLP-1 and its analogs, conjugation at the N-terminus should provide needed protection against DPP-IV, a protease that cleaves residues His7-Ala8.

Choice of PEG-alkyl Oligomers.

By varying the relative length of the alkane (hydrophobic) and PEG (hydrophilic) components, the amphiphilicity and/or solution structure of the conjugate can be improved. The PEG portion is very flexible in solution and may play an important role in resistance to enzymes. The alkyl portion may enhance absorption in the gut and/or enable interaction with cell membranes. The latter feature may be particularly important when the target is a membrane-bound protein on the cell surface, such as the GLP-1 receptor. Thus, the choice of the oligomer may determine the effectiveness of the conjugate in terms of enzyme stability and oral bioavailability.

Purification of Conjugates.

The reaction mixtures are purified on a preparative HPLC column (C-18) with a solvent gradient system made of isopropanol/water (0.1% trifluoroacetic acid). The solvent is evaporated and lyophilized to give dry products. Purity of the conjugates is determined by reversed-phase HPLC and mass spectrometry.

Methods for Activating Oligomeric Moieties

The present example describes methods by which an oligomeric moiety of the present invention may be activated.

Method I—Activation Using DSC

Alkyl-PEG-OH, I (0.4 mmol, 1 eq.) was dissolved in acetonitrile (5 mL) and disuccinimidyl carbonate (DSC, 0.6 mmol, 1.5 eq.) was added. Then triethylamine (1.2 mmol, 1.5 eq.) was added dropwise and after 10 min the reaction mixture became clear. Reaction was stirred overnight at RT. After stirring for ~16 h, the crude reaction was evaporated to dryness and then dissolved in sat. NaHCO$_3$ (10 mL), washed ethyl acetate (2×20 mL), was dried over MgSO$_4$, and evaporated to dryness. Column chromatography (silica, EtOAc/MeOH, 10:1) afforded the activated oligomer II.

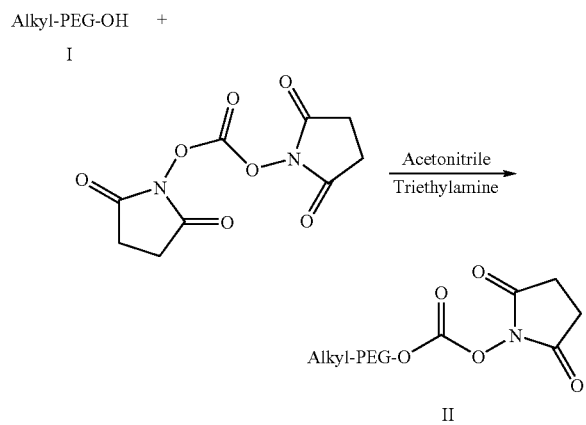

Method II: Activation Using NHS

MPEG-alkyl-acid 1 (0.544 mmol, 1.0 eq.) was dissolved in 15 ml of anhydrous methylene chloride and then solution of N-hydroxysuccinimide (0.816 mmol, 1.5 eq.) and 1-ethyl-3-(3'-dimethylaminopropyl)carbodiimide. HCl (EDCI.HCl, 0.816 mmol, 1.5 eq.) in anhydrous methylene chloride was added. Reaction was stirred for several hours, then washed with 1N HCl, water, dried over MgSO$_4$, filtered and concentrated. Crude material was purified by flash chromatography (silica, gradient elution: 2-5% methanol in CHCl$_3$), to afford activated MPEG-alkyl-acid II.

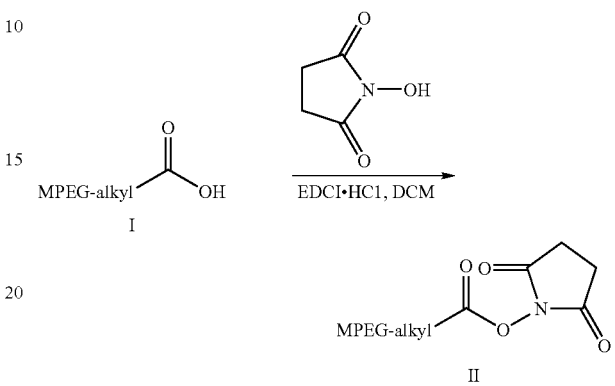

General Procedure for Conjugation to Exenatide

Monoconjugate Exenatide use sites Lys 12, or Lys 27, or at the N-terminus of the peptide.

Method I: Preparation of Monoconjugates

Exenatide (1 equiv) was dissolved in DMSO (1 ml/35 mg of Exenatide). The activated oligomer (1.1 equiv) was dissolved in a minimal amount of THF and added to the solution of Exenatide in DMSO. The reaction was monitored by HPLC. Samples for HPLC monitoring were prepared by taking 50 µL of the reaction and diluting it in 500 µL of H$_2$O containing 0.1% TFA. Reactions were carried out for 180 min. If reactions were not immediately purified they were frozen until purification could be performed.

Method II: Preparation of Multiple Conjugates

Exenatide (1 equiv) was dissolved in DMSO (1 ml/35 mg of Exenatide). Once Exenatide was dissolved, TEA (120 equiv) was added and the solution stirred for 5 min. Then the activated oligomer (2.2 equiv for diconjugate, 4 equiv for triconjugate) was dissolved in a minimal amount of THF and added to the solution of Exenatide in DMSO. The reaction was monitored by HPLC. Samples for HPLC monitoring were prepared by taking 50 µL of the reaction and diluting it in 500 µL of H$_2$O containing 0.1% TFA. Reactions were carried out for 45 min. If reactions were not immediately purified they were frozen until purification could be performed.

Diconjugate of Exenatide use sites Lys 12, and Lys 27, or Lys 12 and N-terminus, or Lys 27 and N-terminus site on Exenatide. Triconjugate Exenatide use sites Lys 12, Lys 27 and N-terminus.

Purification of Conjugates.

The reaction mixtures are purified on a preparative HPLC column (C-18) with a solvent gradient system made of acetonitrile/water (0.1% trifluoroacetic acid). The solvent is evaporated and lyophilized to give dry products. Purity of the conjugates is determined by reversed-phase HPLC and mass spectrometry.

General Procedure for Conjugation to GLP-1
Method I: Preparation of Monoconjugates

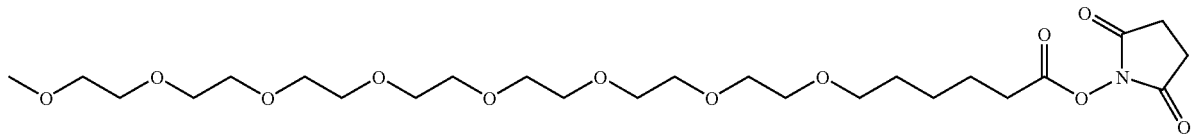

GLP-1 (7-36) amide (1 equiv) was dissolved in 50 mM sodium acetate buffer pH=4 (1 ml/15 mg of GLP-1 (7-36) amide). The pH was adjusted to pH=5.6 with 1M sodium hydroxide. The activated oligomer 1 (1.5 equiv) was dissolved in a minimal amount of acetonitrile and added to the buffered solution of GLP-1 (7-36) amide. The reaction was monitored by HPLC. Samples for HPLC monitoring were taken directly from the reaction mixture in volumes of 40 µL. Reactions were carried out for 6 h. If reactions were not immediately purified they were frozen until purification could be performed.

The reaction mixtures were purified on a preparative HPLC column (C18) with a solvent gradient system made of acetonitrile/water (0.1% trifluoroacetic acid). The solvent was evaporated and lyophilized to provide the conjugates as dry powders. Purities of the conjugates were determined by reverse-phase HPLC and mass spectrometry.

Peptide Mapping

A solution of GLP-1 (7-36) amide (1 mg/mL) and solutions of the purified conjugates (1 mg/mL) were prepared. Samples for peptide mapping were prepared in the following manner. To a vial was added water (60 µL), 1M tris-HCl buffer, pH=9 (20 µL), GLP-1 (7-36) amide or GLP-1 conjugates (100 µL of a 1 mg/mL solution), lysyl endopeptidase (20 µL of a 0.3 mg/mL solution). Reaction was stirred for 1 h then the fragments from the digestion were collected by HPLC and sent for mass spectrometry. In reference to order of elution by HPLC, the first monoconjugate (M1) is located at the N-terminus, the second monoconjugate (M2) is located at the Lys 34, and the third monoconjugate is located at the Lys 26 position.

Method II: Preparation of Multiple Conjugates

GLP-1 (7-36) amide (1 equiv) was dissolved in 50 mM sodium acetate buffer pH=4 (1 ml/15 mg of GLP-1 (7-36) amide). The pH was adjusted to pH=5.6 with 1M sodium hydroxide. The activated oligomer 1 (1.5 equiv) was dissolved in a minimal amount of acetonitrile and added to the buffered solution of GLP-1 (7-36) amide. The reaction was monitored by HPLC. Samples for HPLC monitoring were taken directly from the reaction mixture in volumes of 40 µL. Reactions were carried out for 6 h. If reactions were not immediately purified they were frozen until purification could be performed.

Predominant diconjugate of GLP-1 observed uses sites N-terminus and Lys 34. Triconjugate of GLP-1 uses sites N-terminus, Lys 34 and Lys 26.

Demonstrating Agonist Activity at the GLP-1 Receptor In Vitro

The binding of exenatide or GLP-1 to the GLP-1 receptor results in the production of cAMP, which mediates the physiological effects of the peptide. A cell based cAMP assay is utilized to screen conjugates of the present invention for biological activity in vitro. The in vitro assay is conducted as follows. Media is removed from flask(s) of RIM5F (ATCC) cells and washed once with sterile PBS (Sigma D5837). All PBS is removed, 2 mL of 0.05% trypsin is added, and cells are placed back in the incubator at 37° C. and 5% C02. Once cells have released from the flask, they are resuspended in a total volume of 10 mL. 25 µL is removed and placed in a tube with 75 µL trypan blue and then a 25 µL aliquot is taken and placed on a hemacytometer so that the cells can be counted. The 4 corner blocks of both sides are counted and the final number is divided by 2. That final number is the number of cells times $10^4$/mL. After determining the number of cells needed, 1.5× $10^4$ cells are plated per well (200 µl/well) in a 96 well plate (VWR 29442-056). The cells are placed in an incubator at 37° C. and 5% $CO_2$, and allowed to grow for 48 hours or to near confluence. All media is removed from each well and the cells are washed once with PBS. 90 µL of Prestim Buffer is added to each well and the cells are allowed to sit in the Prestim Buffer for at least 10 minutes prior to dosing. Prestim Buffer is Krebs Ringer+15 nM Sodium Bicarbonate+IBMX to a final concentration of 0.5 mM. The cells are dosed with 10 µL of the following dosages of drug: 1000, 200, 40, 8, 1.6, 0.32, 0.064, and 0 nM drug. Final concentrations of drug are 100, 20, 4, 0.8, 0.16, 0.032, 0.0064, and 0 nM drug. The cells are placed in an incubator at 37° C. with 5% $CO_2$ for fifteen minutes. After a one hour incubation, 100 µL of Assay/Lysis buffer found in the Applied Biosystems cAMP ELISA kit (Molecular Device) is added to the cells and the cells are placed back in the incubator for 30 minutes.

The standards are prepared as follows. 30 mM cAMP calibrator is diluted in cAMP Assay Buffer to prepare stock calibrators of 10000, 100, 33, 11, 3.7, 1.2, and 0.4 nM cAMP. These give 3300, 33, 11, 3.7, 1.2, 0.41, and 0.14 nM (200, 2, 0.67, 0.22, 0.074, 0.025, and 0.008 pmol) final values in the assay. 20 mL of the appropriate concentration of Calibrator working solution is added. 20 mL of samples to be analyzed is placed in appropriate wells. 20 mL of reconstituted Rabbit anti-cAMP Antibody is added to all wells except any reserved for no antibody controls, to which 20 mL assay buffer is added in place of antibody. Plate is placed on a shaker for 5 minutes or gently agitated by hand to ensure mixing. 20 mL reconstituted HRP-cAMP Conjugate is added to every well. This is mixed well and allowed to incubate 2 hours at room temperature. Plate contents are aspirated and washed 4 times with wash buffer, using 80 mL/well with each wash.

Stoplight Red Substrate is prepared as follows. 220 mL of 100× stock Stoplight Red Substrate into is diluted into 22 mL of Substrate Buffer, then 25 mL of 3% $H_2O_2$ (880 mM) is added to bring the final concentration to 0.0034% (1 mM) $H_2O_2$. 50 mL of Stoplight Red substrate is added to every well, minimizing the time between starting and finishing. The plate is covered and left at room temperature for at least 10 minutes, shielded from light. The fluorescence intensity of the plate is read on a luminometer. The data is copied into Soft-Max Pro in order to calculate the amount of cAMP produced. Graph Pad Prizm is used to calculate an $EC_{50}$ for each of the compounds tested.

Demonstrating Increased Resistance to Proteases

Stability against digestive enzymes is critical for proteins and peptides to be delivered orally. It has been previously shown by the present inventor that conjugation of insulin and calcitonin provides protection from proteolytic digestion by trypsin and chymotrypsin and thus the present peptide conjugates are resistance to proteolysis from gastric and intestinal enzymes.

In Vitro Gastric Stability Assay.

Stability of the conjugates in the stomach is demonstrated by exposing the conjugates to digestion by pepsin. The assay is run by incubating the conjugates at 37° C. in the presence of 3 U of pepsin in simulated gastric fluid (33 mM NaCl, pH 1.2) for 5 to 60 minutes. Digestion is stopped by raising the pH of the sample to 7.5. HPLC analysis is used to follow the rate of proteolysis. Area under absorbance peaks (215 nm) is integrated to determine the percent of remaining compound at each time point.

In Vitro Intestinal Stability Assay

The stability of exenatide or GLP-1 conjugates in the intestinal environment is demonstrated by examining the proteolysis of compounds in the presence of trypsin, chymotrypsin and/or elastase. Conjugates are incubated with an enzyme for 2 to 120 minutes at 37° C. Digestions are stopped by adding a 1:1 1% trifluoroacetic acid (TFA): isopropanol quenching solution. Digestion of the conjugates is compared to the digestion of parental compound in each experiment. HPLC analysis of the samples is used to measure the percentage of remaining compound.

In Vitro Systemic Stability Assay

GLP-1 and GLP-1 conjugates (100 μL, 5 nmol/L) were prepared in triethylamine.HCl buffer (10 mmol/L; pH 7.4). DPP-IV (5 mU, 900 μL) was added and the reactions were incubated at 37° C. Samples (100 μL) were quenched by the addition of 5 μL of 10% (v/v) TFA and analyzed by HPLC and ESI-MS. Time points were taken over a period of four hours.

Demonstrating Activity after Oral Administration

Conjugates of exenatide or GLP-1 according to embodiments of the present invention can induce the metabolic effects that are associated with the native peptide. A conjugated exenatide or GLP-1 that can be delivered orally (instead of by repeated injections) is expected to improve patient compliance and perhaps delay the dependence on exogenous insulin for a patient with Type 2 diabetes.

Glucose Lowering Effects of GLP-1 Conjugates in Sprague-Dawley Rats

The purpose of this study is to evaluate the Glucose lowering effects of GLP-1 conjugates in Sprague-Dawley rats. Male Sprague Dawley rats with body weights between 225-250 g will be used in this study. Animals will be purchased from Charles River Laboratories, Raleigh, N.C. and be given at least 48 hours to acclimate before study initiation. Animals will be housed in plastic cages (n=3/cage/sex) and kept in a room with a 12 hour light/dark cycle. Food and water will be provided ad libitum throughout the acclimation period. The animals will be fasted 12 h and will be presented food for a period of 30 minutes prior to experiment.

Experimental Procedures:

The animals are injected subcutaneously with ether vehicle or GLP-1 conjugates or Exenatide conjugates. Five animals are injected in each group. The glucose and insulin level is measured at −30, 0, 30, 60, 120, 180, 240, and 360 minutes.

REFERENCES

The contents of all references and patents cited herein are hereby incorporated by reference herein for all purposes.

Barragan, J. M., R. E. Rodriguez, et al. (1996). "Interactions of exendin-(9-39) with the effects of glucagon-like peptide-1-(7-36) amide and of exendin-4 on arterial blood pressure and heart rate in rats." *Regulatory Peptides* 67(1): 63-68.

Eng, J. and C. Eng (1992). "Exendin-3 and Exendin-4 Are Insulin Secretagogues." *Regulatory Peptides* 40(2): 142-142.

Eng, J., W. A. Kleinman, et al. (1992). "Isolation and Characterization of Exendin-4, an Exendin-3 Analog, from Heloderma-Suspectum Venom—Further Evidence for an Exendin Receptor on Dispersed Acini from Guinea-Pig Pancreas." *Journal of Biological Chemistry* 267(11): 7402-7405.

Malhotra, R., L. Singh, et al. (1992). "Exendin-4, a New Peptide from Heloderma-Suspectum Venom, Potentiates Cholecystokinin-Induced Amylase Release from Rat Pancreatic Acini." *Regulatory Peptides* 41(2): 149-156.

Tissue and Plasma Concentrations of Amidated and Glycine-Extended Glucagon-Like Peptide I in Humans. *Diabetes*. 1994 April; 43(4):535-9.

Biological Effects and Metabolic Rates of Glucagonlike Peptide-1 7-36 Amide and Glucagonlike Peptide-1 7-37 in Healthy Subjects are Indistinguishable. *Diabetes*. 1993 May; 42(5):658-61.

Minireview: The Glucagon-Like Peptides. *Endocrinology*. 2001 February; 142(2):521-7.

Development of Glucagon-Like Peptide-1-Based Pharmaceuticals as Therapeutic Agents for the Treatment of Diabetes. *Curr Pharm Des*. 2001 September; 7(14):1399-412.

Biological Actions and Therapeutic Potential of the Glucagon-Like Peptides. *Gastroenterology*. 2002 February; 122(2):531-44.

Glucagon-Like Peptide 1 and its Derivatives in the Treatment of Diabetes. *Regulatory Peptides*. 2005 July; 128:135-48.

Synthesis, Characterization, and Pharmacokinetic Studies of PEGylated Glucagon-like Peptide-1. *Bioconjugate Chem*. 2005, 16, 377-382.

Both Subcutaneously and Intravenously Administered Glucagon-like Peptide I are rapidly degraded from the NH2-terminus in Type II Diabetic Patients and in Healthy Subjects. *Diabetes*. 1995 September; 44(9):1126-31.

That which is claimed is:

1. A metabolic compound conjugate comprising:
   (a) a metabolically active peptide GLP-1 agonist selected from the group consisting of GLP-1, and exenatide, wherein the metabolically active peptide GLP-1 agonist comprises:
      (i) a glucagon-like peptide (GLP-1) receptor binding motif having affinity for the GLP-1 receptor; and
      (ii) at least one oligomer conjugation site, wherein the oligomer conjugation site is an amino acid residue; and
   (b) an amphiphilic oligomer attached to the at least one oligomer conjugation site, wherein the oligomer has a formula:

$$-C(O)-(CH_2)_m-X(C_2H_4O)_n-Y \quad \text{(Formula X)}$$

wherein m is 2-10; and n is 2-16; and, X is —C—, —O—, —C(O)—, —NH—, —NHC(O)—, or —C(O)NH—; and Y is lower alkyl or —H, wherein when the metabolically active peptide GLP-1 agonist is exenatide the oligomer is conjugated as a monoconjugate at the N-terminus, $Lys^{12}$, or $Lys^{27}$, or di-conjugates at N-terminus/$Lys^{12}$, $Lys^{12}$/$Lys^{27}$ or N-terminus/$Lys^{27}$, and wherein when the metabolically active peptide GLP-1 agonist is GLP-1 comprising SEQ ID NO: 1 or SEQ ID NO: 2, the oligomer is conjugated as a monoconjugate at the N-terminus, $Lys^{20}$, or $Lys^{28}$, or di-conjugates at N-terminus/$Lys^{20}$, $Lys^{20}$/$Lys^{28}$ or N-terminus/$Lys^{28}$.

2. The metabolic compound conjugate according to claim 1, wherein the metabolic compound conjugate exhibits one or more advantages selected from the group consisting of increased resistance to enzymatic degradation relative to a corresponding unconjugated metabolic compound, increased circulating half life, increased bioavailability, and prolonged duration of effect.

3. The metabolic compound conjugate according to claim 1 wherein the metabolic compound comprises a GLP-1 sequence.

4. The metabolic compound conjugate according to claim 1, wherein the metabolic compound comprises an exenatide sequence.

5. The metabolic compound conjugate according to claim 1, further comprising a pharmaceutically acceptable carrier thereby providing a pharmaceutical composition.

6. A method of treating a condition characterized by an excessive level of glucose in the blood, the method comprising administering to a subject in need thereof a pharmaceutically acceptable amount of a metabolic compound conjugate of claim 1.

7. The method of claim 6, wherein the pharmaceutically acceptable amount of a metabolic compound conjugate is administered orally or perorally.

* * * * *

SEQUENCE LISTING

```
<160> NUMBER OF SEQ ID NOS: 4

<210> SEQ ID NO 1
<211> LENGTH: 30
<212> TYPE: PRT
<213> ORGANISM: Artificial Sequence
<220> FEATURE:
<223> OTHER INFORMATION: Synthetic construct
```

```
<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic construct

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 39
<212> TYPE: PRT
<213> ORGANISM: Artificial
<220> FEATURE:
<223> OTHER INFORMATION: Synthetic construct

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic Construct

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```